(12) United States Patent
Lupien

(10) Patent No.: US 8,278,799 B1
(45) Date of Patent: Oct. 2, 2012

(54) SYSTEM AND METHOD FOR OPTIMIZING THE DESIGN OF AN ULTRASONIC TRANSDUCER

(76) Inventor: Vincent Lupien, Wakefield, MA (US)

(*) Notice: Subject to any disclaimer, the term of this patent is extended or adjusted under 35 U.S.C. 154(b) by 325 days.

(21) Appl. No.: 12/642,306

(22) Filed: Dec. 18, 2009

Related U.S. Application Data

(62) Division of application No. 11/191,479, filed on Jul. 27, 2005, now abandoned.

(60) Provisional application No. 60/591,567, filed on Jul. 27, 2004.

(51) Int. Cl.
*H01L 41/04* (2006.01)
(52) U.S. Cl. ........ 310/334; 310/335; 310/336; 310/337; 73/633; 703/5; 600/439
(58) Field of Classification Search .......... 310/334–337; 73/633; 703/5; 600/439
See application file for complete search history.

(56) References Cited

U.S. PATENT DOCUMENTS

| | | | | |
|---|---|---|---|---|
| 5,844,140 A * | 12/1998 | Seale | | 73/633 |
| 6,002,914 A * | 12/1999 | Weinberg | | 434/6 |
| 6,057,632 A * | 5/2000 | Ustuner | | 310/334 |
| 6,719,694 B2 * | 4/2004 | Weng et al. | | 600/439 |
| 7,006,955 B2 * | 2/2006 | Daft et al. | | 703/5 |
| 7,230,368 B2 * | 6/2007 | Lukacs et al. | | 310/335 |
| 7,245,063 B2 * | 7/2007 | Lupien et al. | | 310/334 |
| 7,830,069 B2 * | 11/2010 | Lukacs et al. | | 310/334 |
| 2003/0154062 A1 * | 8/2003 | Daft et al. | | 703/5 |

* cited by examiner

*Primary Examiner* — Tse Chen
*Assistant Examiner* — Baisakhi Roy
(74) *Attorney, Agent, or Firm* — Joseph Stecewycz

(57) ABSTRACT

A system and method for determining optimal values for the geometrical features of an ultrasonic transducer having one or more elements, the method including backprojection raytracing to determine the parameters required for apertures located on an ultrasonic probe surface. The ultrasonic probe design system includes an interface for inputting statement parameters, insonification requirements, and geometric constraints, with an engine responsive to the interface and configured to determine and provide an optimized transducer geometric design output.

11 Claims, 17 Drawing Sheets

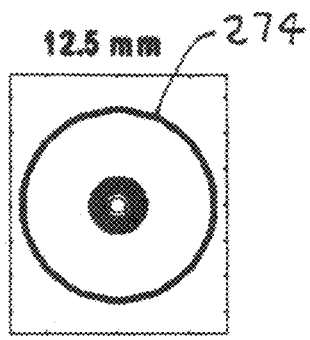
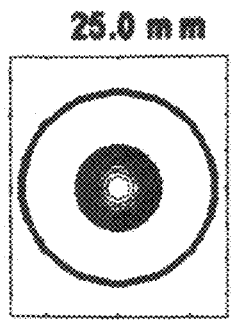
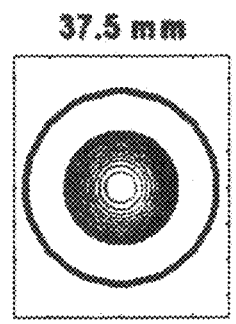
Fig. 19A     Fig. 19B     Fig. 19C
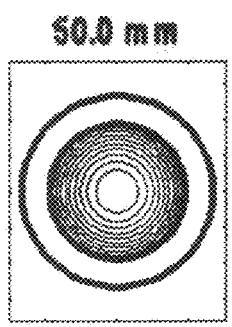
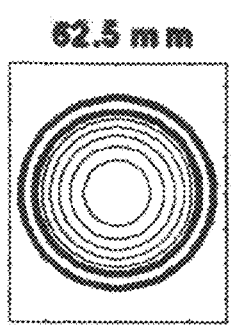
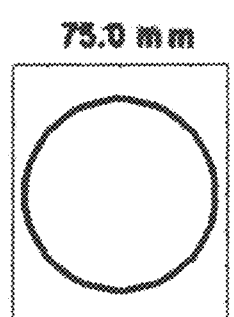
Fig. 19D     Fig. 19E     Fig. 19F
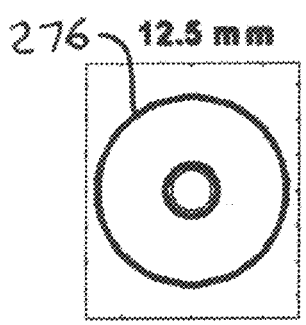
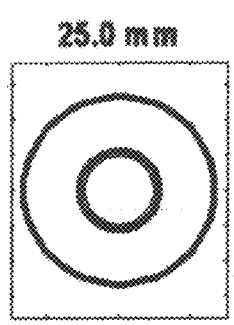
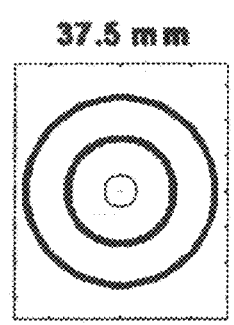
Fig. 20A     Fig. 20B     Fig. 20C
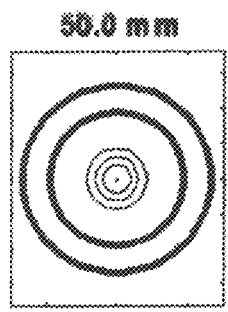
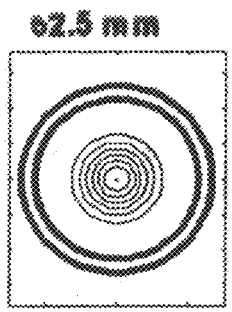
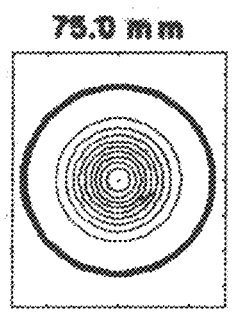
Fig. 20D     Fig. 20E     Fig. 20F

SYSTEM AND METHOD FOR OPTIMIZING THE DESIGN OF AN ULTRASONIC TRANSDUCER

CROSS-REFERENCE TO RELATED APPLICATION

The present Application is related to Provisional Patent Application entitled "System and method for optimizing the design of a phased array ultrasonic probe" filed 27 Jul. 2004 and assigned Ser. No. 60/591,567 and is a divisional of patent application Ser. No. 11/191,479 filed 27 Jul. 2005 now abandoned.

BACKGROUND OF THE INVENTION

1. Field of Invention

This invention relates to a system and method for designing ultrasonic transducers and, in particular, to a system and method for determining optimal values for the geometrical features of an ultrasonic transducer having one or more elements.

2. Description of the Background Art

Ultrasonic transducers containing one or more independently controlled transducer elements are commonly used in the fields of non-destructive testing, medical imaging, medical therapy, flow meters and sonar. Such transducers may be used in conjunction with one or more acoustic lenses and/or one or more acoustic mirrors to achieve a desired ultrasonic insonification. No single transducer design can meet the needs of all the applications of ultrasound, even when such applications are categorized in a single field. For this reason, it is commonplace to design ultrasonic transducers, along with any associated lenses or mirrors, specifically for each application.

Classical single element ultrasonic transducers can usually be adequately specified using a small number of parameters, typically limited to the transducer's diameter, center frequency, and focusing distance. These parameters are often straightforward to determine based on the desired beam spot size in the material to be insonified, the desired focusing location in the material, the ultrasonic velocity in the material, the standoff distance from the surface of the material, if any, and the ultrasonic velocity in the coupling medium, if any.

In contrast, modern array transducers contain several elements. Their specification requires additional parameters including the number of elements and the size and shape of each element. Instead of a single focal point, an array transducer can generate a variety of focal points in different directions, and can adapt to varying material properties and geometries, making the determination of the transducer parameters more difficult.

Modern ultrasonic transducer manufacturing techniques, such as those based on piezocomposite technology, allow arbitrarily shaped conventional and array transducers to be manufactured to high accuracy relative to the ultrasonic wavelength. This added flexibility has further increased the complexity of specifying the parameters necessary for transducer manufacture.

In response to these new challenges in ultrasonic transducer design, approaches and tools have emerged in the relevant art to assist in the transducer development process. For example, several commercially available software packages exist which can be used to numerically simulate the ultrasonic energy radiated by candidate transducer designs. Such software packages are highly valuable to verify that the proposed transducer meets all the performance criteria before the considerable expense of transducer manufacture is undertaken.

The paper entitled "Ultrasonic Phased Array Inspection of Titanium Billets" (Lupien, Vincent and Cancre, Fabrice, *Review of Progress in Quantitative Nondestructive Evaluation*, Vol. 20, Edited by Thompson and Chimenti, AIP Conference Proceedings, 2001), listing the applicant as a co-author, hereof presents a method to establish the ring and sector boundaries of an annular-sectorial transducer array used for the inspection of titanium cylinders used in the aircraft engine industry. The shape of the array is prescribed to be that which produces spherical focusing at the deepest focusing point inside the cylinder. This paper is incorporated herein by this reference.

The paper entitled "High Sensitivity Inspection of Titanium Forgings in the ETC Program: Probe Design and Implementation" (Roberts, Ron, *Phased Array Ultrasound for Aerospace Applications Workshop*, University of Dayton Research Institute, 2004), presents a custom designed ultrasonic array transducer for use with an ultrasonic mirror. The ultrasonic transducer is targeted to engine disk inspection and makes use of a more advanced shape composed of three concentric regions with distinct radii of curvature. The three curvature design was proposed to help reduce the number of rings on the transducer.

In prior art such as the papers cited above, the transducer design must be performed by a skilled expert based on physical knowledge, judgment, intuition and considerations of practical issues, along with verification that the design is valid through repeated numerical modeling, numerical simulations and laboratory experimentation. This design process is both time consuming and lacking in consistency. A great number of distinct valid transducer designs can exist other than the ones proposed by the designers. The specific transducer designs achieved depend on the talent of the designer and the ad hoc design method used. The transducer design cannot be ascertained to be optimal in any real sense. For example, other valid designs may exist which require fewer transducer elements. Since the cost of the probes and driving electronics both increase with the number of elements in the transducer, it is usually desirable to achieve a transducer design that minimizes the number of elements. Alternatively, space constrained ultrasonic applications may benefit from the minimization of the size of the transducer.

While the state of the art provides means to achieve designs which are adequate, what is lacking is a more scientific method of ensuring that optimal transducer designs are obtained and can achieve more consistent results.

SUMMARY OF THE INVENTION

It is therefore an object of this invention to provide a system and method for optimizing the Geometrical Design of an ultrasonic transducer array that may include associated lenses or mirrors.

It is a further object of this invention to provide such a system and method which automates some of the Geometrical Design processes for a custom transducer array system including any associated lenses or mirrors.

It is a further object of this invention to provide such a system and method which reduces the modeling, the experimentation, and the application of engineering judgment associated with prior methods of obtaining Geometrical Designs of ultrasonic transducer arrays.

It is a further object of this invention to provide such a system and method that yields consistent results.

It is a further object of this invention to reduce the level of expertise in ultrasonic physics necessary for producing valid Geometrical Designs of ultrasonic transducers.

The invention results from the realizations that, a cost function can be calculated representative of the aspects of the ultrasonic field and Geometric Design of an ultrasonic transducer which are to be minimized based on (i) inputs associated with the specified Basic Problem Statement, (ii) Insonification Requirements, and (iii) Geometrical Constraints, and that by iteratively evaluating different transducer geometrical designs to minimize the cost function, an optimized geometrical design may be obtained without requiring conventional methods of experimentation and judgment determinations.

The terms Basic Problem Statement, Insonification Requirement, Geometrical Constraint and Geometrical Design have specific meaning within the context of the present invention and are defined in the Detailed Description of the Invention.

DESCRIPTION OF THE DRAWINGS

FIGS. 19A-F are illustrations of the required phase variation at six focusing depths for the Fermat focused probe of FIG. 17;

FIGS. 20A-F are illustrations of the required phase variation at six focusing depths for the probe design computed in accordance with the process flow diagram steps of FIG. 16;

DETAILED DESCRIPTION OF THE INVENTION

Figure 1:
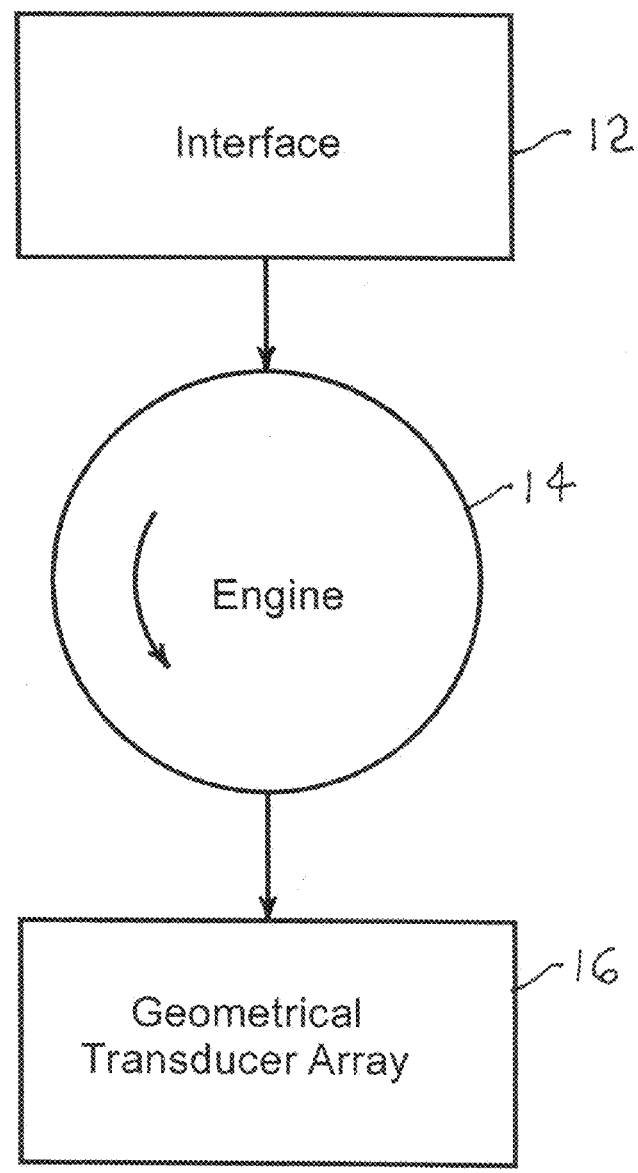
FIG. 1 is a block diagram depicting an engine disposed between an interface and a geometrical transducer array comprising a system for optimizing the Geometrical Design of an ultrasonic transducer array in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

The disclosed method comprises a Basic Problem Statement which includes one or more media through which ultrasound will propagate and their relevant physical properties, the volume of interest for insonification within the material or materials, and the geometry of the boundaries of the material or materials. Included among the media may be one or more media used for ultrasonic coupling. The physical properties of each medium may include one or more of the following: the density of the medium, the attenuation of the medium, the longitudinal and/or shear sound speeds of the medium, the shape of the medium, the anisotropy of the medium, the homogeneity of the medium, and/or the scattering properties within the medium and other relevant physical properties. The array of physical properties of each medium is represented by the symbol $\vec{\gamma}$.

Figure 3:
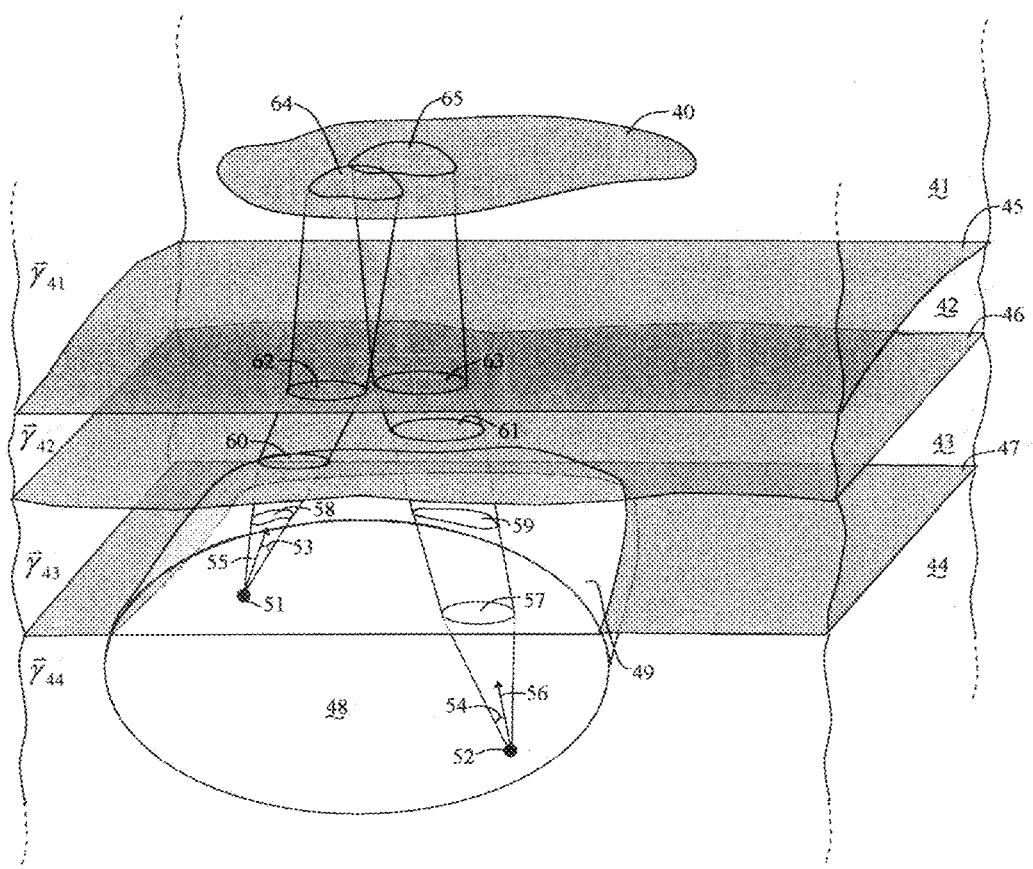
FIG. 3 is a diagrammatical depiction of the main aspects of a Basic Problem Statement and Insonification Requirements for a transducer Geometrical Design problem involving two coupling media and a volume of interest lying within two other media.

The concept of a Basic Problem Statement is illustrated in the example ultrasonic insonification scenario of FIG. 3. A volume of interest 48 is bounded by surface 49 embedded in two media 43 and 44 having physical properties $\vec{\gamma}_{43}$ and $\vec{\gamma}_{44}$, with no mirrors or lenses.

Boundary surface 47, shown here to be a flat plane but which could be arbitrarily shaped, separates media 43 and 44. In order to access volume of interest 48 from transducer surface 40, ultrasound must pass through coupling media 41 and 42, having physical properties $\vec{\gamma}_{41}$ and $\vec{\gamma}_{42}$. Boundary surface 45, shown here to be curved, separates media 41 and 42 and boundary surface 46 shown to be curved separates media 42 and 43.

Figure 4:
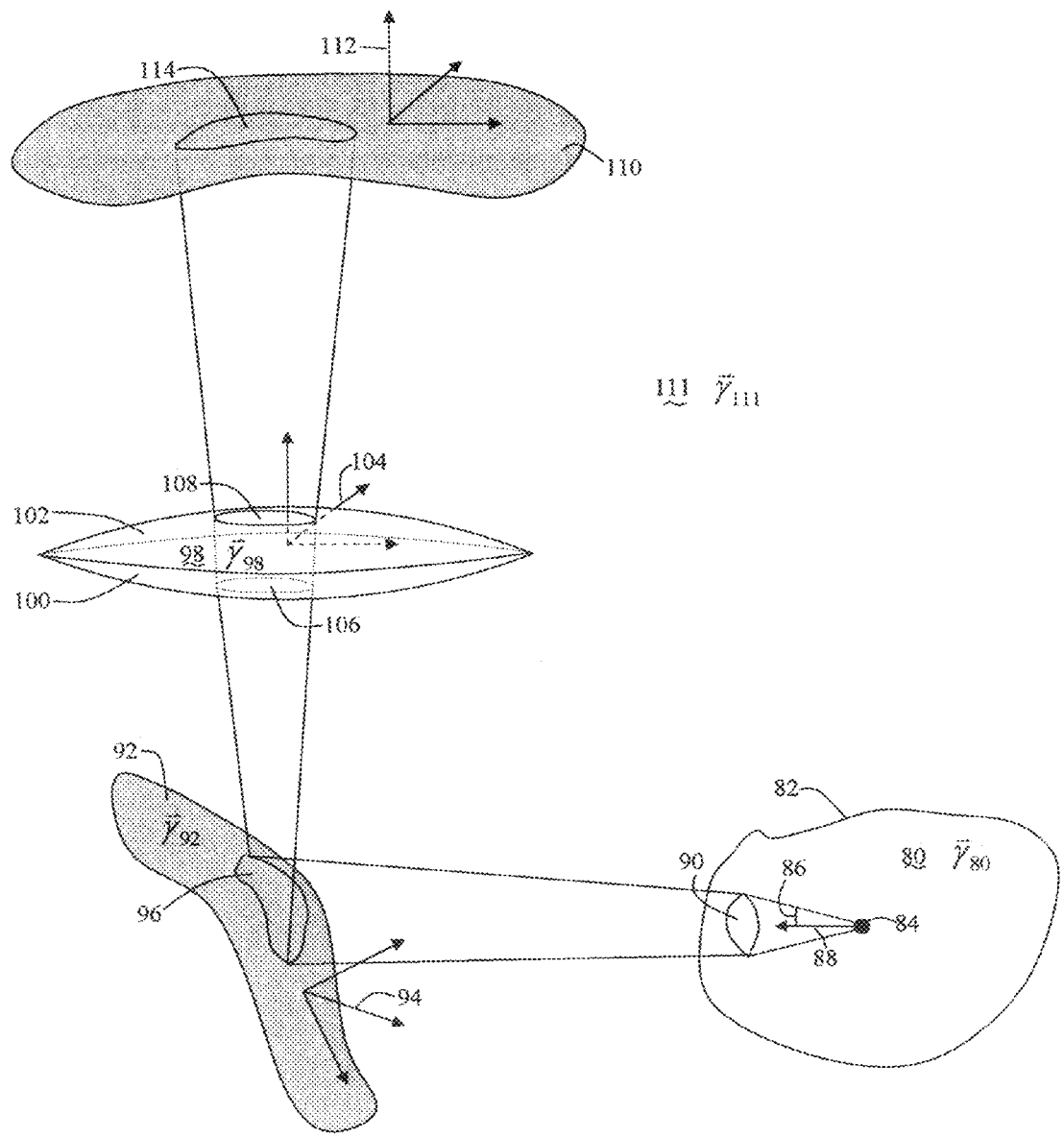
FIG. 4 is a diagrammatical depiction of the main aspects of a Basic Problem Statement and Insonification Requirements for a transducer Geometrical Design problem involving a volume of interest within one medium, and one coupling medium, one mirror and one lens.

There is shown in FIG. 4 a diagrammatic representation of another insonification scenario to further illustrate the concept of a Basic Problem Statement in the case where lenses and/or mirrors are used. The volume of interest in this example is the entirety of medium 80, bounded by surface 82 and having physical properties $\vec{\gamma}_{80}$. In the coupling medium 111 having physical properties $\vec{\gamma}_{111}$ are contained a mirror 92 having physical properties $\vec{\gamma}_{92}$ and lens 98 having physical properties $\vec{\gamma}_{98}$ which both lie in the path of ultrasound as it travels from transducer surface 110 to points such as 84 within volume of interest 80. Changes in the number of lenses or mirrors with respect to the example of FIG. 4, or in their arrangement along the ultrasonic path are seen to lie within the scope of the invention.

In detection applications, additional physical and geometrical properties corresponding to the targets or defects to detect may be provided as part of the Basic Problem Statement. These additional physical properties may include the size and shape distribution of the defects, the density of the defects, the longitudinal and/or shear sound speeds of the defects, the roughness of the defect surface and the porosity of the defects. Similarly, in imaging applications, additional physical properties may be provided about the structures to be imaged. In therapeutic and other non-diagnostic uses of ultrasound, additional information may be provided about the tissues or objects to influence or destroy.

To further illustrate specification of the Basic Problem Statement, consider the inspection of cylinders, or billets, of titanium for the aircraft engine industry. The known shear and longitudinal sound speeds of titanium and the sound speed of the coupling medium, water, constitute sufficient physical properties to obtain optimized Geometrical Designs minimizing the number of elements in the transducer according to the present invention. The volume of interest may be the entire volume of the billet, which must be inspected for different types of inclusions including hard alpha inclusions. The radius and length of the cylinder constitute the definition of the geometry of the boundaries of the titanium. Information on the targets or inclusions to be detected may be specified through known or estimated material and ultrasonic properties of the inclusions, as well as their expected size and shape distributions, and ultrasonic scattering properties. As should be clear to those skilled in the art, similar illustrative examples can be found for Basic Problem Statements in flow meter, medical imaging, medical therapy and sonar applications.

Once this Basic Problem Statement has been formulated, the design of the transducer, lenses, mirrors or any combination thereof proceeds to the specification of Insonification Requirements, which include information about the desired ultrasonic field in the volume of interest. Typical Insonification Requirements include one or more focusing points or ranges in the medium, one or more beam directions, angular or spatial beamwidths associated with the focusing points, ranges and/or beam angles, sidelobe level requirement, grating lobe level requirements, requirements on the symmetry and uniformity of the beam, and other characteristics of the field. Also included in the Insonification Requirements may be scanning requirements detailing any planned physical motion of the transducer and any associated lenses or mirrors across the material or materials to aid in achieving the desired coverage specified in the volume of interest or to expand the number of angles at which the points within the volume of interest may be accessed.

The Insonification Requirements may also include the desired impulse/frequency response, or some subset of it such as one or more of the following: center frequency, bandwidth, pulse type, pulse amplitude, pulse duration and other simplified measures of impulse response. In applications where ultrasound is transmitted and subsequently received by the same or another transducer, the Insonification Requirements are not specific to either the transmit operation or the receive operation. That is, a separate set of Insonification Requirements may be specified for each operation. The set of Insonification Requirements is established based on the designer's best effort at meeting the Basic Problem Statement, and is typically the result of an iterative process involving any one or more of the following: judgment, past experience, numerical modeling and simulation, laboratory experimentation and consideration of practical issues.

As a simple example of specifying Insonification Requirements, consider FIG. 3. Within volume of interest 48 in medium 43 there is shown a focusing point 51 at position $\vec{r}_{51}$ requiring insonification with a cone of ultrasound having half angle 53, $\beta_{53}$, and reversed mean incident unit vector 55, $\vec{r}_{55}$. Similarly, within volume of interest 48 and in medium 44 there is shown a focusing point 52 at position $\vec{r}_{52}$ requiring insonification with a cone of ultrasound having half angle 54, $\beta_{54}$, and reversed mean incident unit vector 56, $\vec{r}_{56}$. Requirements on the impulse/frequency response are not shown in FIG. 3; these may be determined separately by the designer based on knowledge of the application to complete specification of the Insonification Requirements.

In FIG. 4, within volume of interest 80 which is also the medium, there is shown a focusing point 84 requiring insonification with a cone of ultrasound having half angle 86 and reversed mean incident unit vector 88. Requirements on the impulse/frequency response are not shown in FIG. 4; these may be determined separately by the designer based on knowledge of the application to complete specification of the Insonification Requirements.

It may be desirable to specify the Insonification Requirements continuously throughout the volume of interest V rather than as a set of discrete points. In such a case quantities such as the cone half angles and incident vectors can be specified as continuous functions of space $\beta^j(\vec{r})$ and $\vec{m}^j(\vec{r})$ respectively, for $\vec{r}$ within subvolume $V_j \subseteq V$, An arbitrary number N of potentially overlapping functions) $\beta^j(\vec{r})$ and $\vec{m}^j(\vec{r})$, and subvolumes $V_j \subseteq V$ may be specified within V, i.e. j=1, 2, ..., N. In this manner it is possible to specify that certain locations in the volume of interest require insonification from several different directions and with several different beamwidths.

Optionally, the desired beam diameters $w^j(\vec{r})$ at the focal points can be specified. Corresponding cone half angles $\beta^j(\vec{r})$ can be computed from the beam diameters using the formula, $$\beta^j(\vec{r}) = \arctan\left(\frac{\lambda}{2w^j(\vec{r})}\right) \quad (1)$$

where $\lambda$ is the wavelength in the medium containing the focal point at the center frequency of the inspection beam. Equation (1) remains accurate as long as the focusing point is within the near field and as long as $w^j(\vec{r}) > \lambda/2$.

To further illustrate the specification of Insonification Requirements, consider the inspection of titanium billets. It has been established in prior art that the detection of inclusions within the billet can be achieved by: (i) using the same transducer for transmitting and receiving ultrasound; (ii) using a 5 MHz center frequency pulse of two or three cycle duration and inspecting the billet normal to its surface; (iii) using a 6-dB beamwidth of about 0.100 inches; (iv) maintaining a substantially constant beamwidth from the surface of the billet to its center; and (v) performing a helical scan of the billet by rotating the billet about its axis and moving the transducer in a straight line parallel to the billet axis. As should be clear to those skilled in the art, similar illustrative examples can be found for Insonification Requirements in flow meter, medical imaging, medical therapy and sonar applications.

Upon specification of the Basic Problem Statement and of the Insonification Requirements, the Geometrical Design of the transducer can proceed, where the design process includes obtaining the geometrical features of the transducer and of any associated lens or mirror. These geometrical features include, for example, the position, orientation, shape and boundary of the transducer and of any associated lenses and/or mirrors. In FIG. 3, the Geometrical Design includes determining the transducer surface 40. In FIG. 4, the Geometrical Design includes determining transducer surface 110, the mirror surface 92, the bottom surface 100 of the lens 98 and the top surface 102 of the lens 98.

The geometrical features that are part of the Geometrical Design may also include the number of elements comprising the transducer and the size, shape, position and orientation of each element on the transducer face. One or more geometrical features may be imposed as a constraint. If a geometrical feature is constrained with an equality constraint, the geometrical design process involves determining the remaining geometrical features while still meeting the requirements of the Basic Problem Statement and of the Insonification Requirements. If a geometrical feature is constrained with an inequality constraint, the geometrical design process still must determine the value of the geometrical feature along with the other geometrical features that are part of the Geometrical Design.

Typical geometrical constraints include one or more of: the distance between point(s) on the transducer and point(s) on the surface or within the medium(s), the orientation of the transducer relative to a reference orientation, characteristics of the shape of the transducer such as smoothness and continuity, the number of elements, the size of the elements, the shape of the elements, the shape of the element boundaries, the spacing between the elements, the requirement that the transducer shape lie within certain regions of space, and other geometrical constraints.

For example, in practice the transducer normally lies in a single medium. In FIG. 3, this statement implies that transducer surface 40 must lie entirely in the medium 41. In FIG. 4, transducer surface 110 must lie entirely in the medium 111 and must not collide with the lens 98, mirror 92 or volume of interest 80. In order to prevent the candidate transducer surfaces proposed by the optimization algorithm from colliding with the other media, a geometrical constraint is imposed that any point on the transducer surface cannot be part of any mirror and/or lens surface nor can it part of any medium except the first medium, which is medium 41 in FIG. 3 and medium 111 in FIG. 4.

As another example of a common Geometrical Constraint, consider the distance of the transducer surface from the surface of the volume of interest, which is often part of the previously established ultrasonic approach and is referred to as a standoff distance, water path, or wedge delay. In such cases it is useful to specify a specific point a which must be part of the transducer surface S.

$$\vec{a} \in S. \quad (2)$$

The disclosed method may include framing the Geometrical Design process as a constrained optimization problem with Optimization Attributes consisting of one or more desirable attributes to be maximized and one or more undesirable attributes to be minimized, subject to meeting all the conditions of (i) the Basic Problem Statement, (ii), the Insonification Requirements and (iii) the Geometrical Constraints. Weights may be assigned to each of the desirable and undesirable characteristics to establish their relative importance.

For example, increasing the number of elements in ultrasonic transducers comprising multi-element arrays drives up the cost and manufacturing complexity of both the transducer and the electronics driving the elements. It is therefore desirable to design ultrasonic transducers that minimize the number of elements while satisfying all the Basic, Insonification, and Geometrical requirements. Thus, the number of elements is an attribute of the Geometrical Design which would be minimized according to the present invention.

By coupling the above framework with an optimization method, optimal Geometrical Designs can be obtained directly from the statement of the Basic Problem, Insonification Requirements, Geometrical requirements, and the Optimization Attributes. In this manner, the traditional iterative manual Geometrical Design approach, with its designer dependence and inability to ascertain optimality, is replaced with an automated method yielding more consistent results which are very close to being optimal in the strict mathematical sense. The method of this invention is therefore seen to take the transducer Geometrical Design process from an art to a science. Additionally, the method of this invention functions to simplify the Geometrical Design process, making it accessible to a greater number of experts in ultrasound.

There is shown in FIG. 1 an exemplary embodiment of an ultrasonic probe design system 10 suitable for use in optimizing the design of a phased array ultrasonic transducer, in accordance with the present invention. The ultrasonic probe design system 10 includes an interface 12 for inputting the parameters of (i) the Basic Problem Statement, (ii) the Insonification Requirements and (iii) the Geometric Constraints. Additionally, the interface 12 is used to specify the Optimization Attributes and Weighting Factors to establish the relative importance of the attributes. An engine 14 is responsive to interface 12 and is configured to optimize the Geometrical Design of the array and to determine and provide an optimized transducer Geometric Design output 16.

The engine 14 provides means to compute a numerical value for each of the Optimization Attributes given a candidate Geometrical Design and the underlying Basic Problem Statement, Insonification Requirements, and Geometrical Constraints. Certain possible Optimization Attributes, such as the number of elements, are inherently numerical in nature and are amenable to numerical optimization methods. Other Optimization Attributes, such as the size of the transducer, are more ambiguous. The size of the transducer may be taken to mean the area, perimeter, greatest diameter, or other size-related value. Interface 12 may provide means for specifying such choices unambiguously for the engine 14.

Each of the numerical values can be defined in such a way that it decreases monotonically as the desirability of its corresponding Optimization Attribute increases. The engine 14 may then be configured to produce a Global Cost consisting of the Weighted Sum of the numerical values for each Optimization Attribute. The engine 14 subsequently determines the Geometrical Design of the transducer as that which minimizes the Global Cost subject to the Basic Problem Statement, the Insonification Requirements, and the Geometrical Constraints. Alternatively if any of the numerical values of the Optimization Attributes increase with the desirability of each attribute, the engine 14 may multiply such numerical values by minus one before computing the weighted sum.

Figure 2:
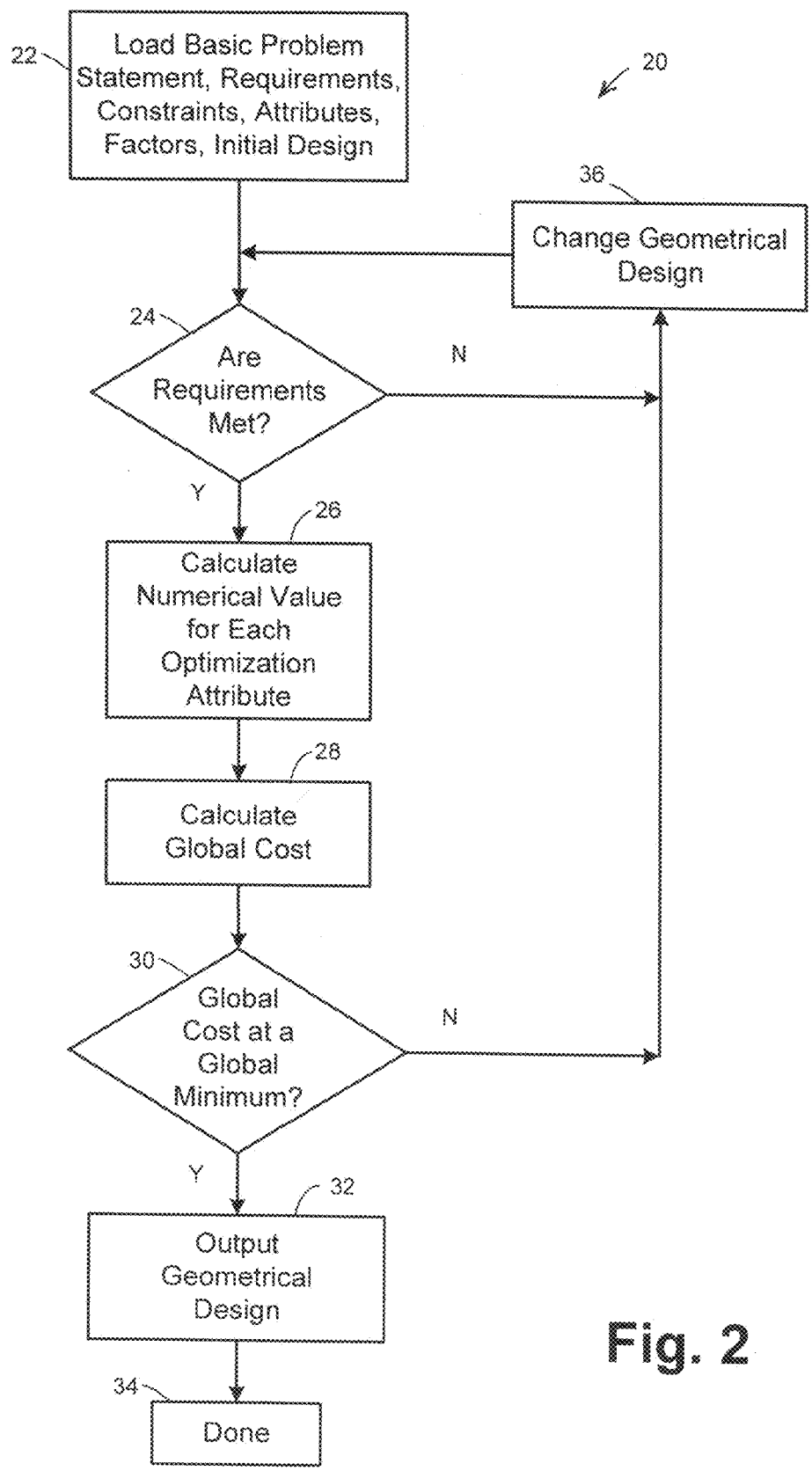
FIG. 2 is a process flow diagram associated with both the system of FIG. 1 and a method for optimizing the Geometrical Design of an ultrasonic transducer array in accordance with the subject invention.

The interface 12 may comprise a data file that includes the physical, geometric and ultrasonic parameters described earlier in the Basic Problem Statement, Insonification Requirements and Geometrical Constraints. In an exemplary embodiment, the engine 14 may comprise computer-readable software for performing a design method, represented by a flow diagram 20 shown in FIG. 2, for designing an ultrasonic array transducer, in accordance with the present invention. At step 22, the engine 14 loads the parameters associated with the Basic Problem Statement, Insonification Requirements, Geometrical Constraints, Optimization Attributes, Weighting Factors and an initial guess of the Geometrical Design. At a first decision block 24, the engine 14 determines whether all the requirements of the Basic Problem Statement, Insonification Requirements and Geometrical Constraints are met by the candidate Geometrical Design. If the requirements are not met, flow control proceeds to step 36, where the Geometrical Design is changed to a new trial value before passing control back to the first decision block 24 again. In order for the Geometrical Design to be changed, all aspects of the Geometrical Design must have been parameterized as discussed below. Blocks 24 and 36 may iterate several times before the requirements are met. Once the requirements are met, a numerical value is computed for each Optimization Attribute in step 26. Preferably, the Weighting Factors are used to compute a Global Cost which is equal to the weighted sum of the Optimization Attributes, in step 28.

The engine 14 is programmed with means to evaluate whether the computed Global Cost is at, or sufficiently close to, a minimum in a second decision block 30. Such means would typically consist of a nonlinear constrained optimization method such as sequential quadratic programming. If a minimum is not achieved at the second decision block 30, or if an insufficient number of trial Geometrical Designs have been evaluated to ascertain whether a minimum has been reached, flow control passes to block 36, which changes the Geometrical Design. Changes in the parameters governing the Geometrical Design are performed according to the selected numerical optimization method. Blocks 36, 24, 26, 28 and 30 are iteratively executed until the minimum of the Global Cost is deemed to have been reached in the second decision block 30, at which point the optimal Geometrical Design is outputted in step 32, signaling the end of the optimization process, at step 34.

In a common embodiment of the invention, the number of elements of the transducer is the only Optimization Attribute. Transducer arrays can possess a one dimensional arrangement of elements, as in linear arrays composed of side by side rectangles and annular arrays composed of concentric rings. Transducer arrays can also possess a two-dimensional arrangement of elements, as in matrix arrays composed of a grid of squares or rectangles, or annular sectorial arrays composed of sectorized rings. Many other more complicated one dimensional and two dimensional arrays are possible.

The unifying concept governing the required number of elements for each of these different types of arrays is that each element on a phased array probe should possess sufficient directivity to access all the required focal points in the Insonification Requirements. Equivalently, one could say that each element should be small enough such that over every focusing point and inspection direction, the phase variation over the element's surface will be lower than a certain threshold. The specific value of threshold is subject to discussion; however, a range between $\pi/8$ and $\pi/6$ radians of phase at the center frequency will ensure constructive summation of the signal over the entire surface of the element even for signals with relatively high bandwidths. Minimizing the number of elements therefore consists in minimizing the rate of phase variation on the transducer surfaces 40 and 110, for example.

The optimization method relies on iteratively changing the parameters of the Geometrical Design and evaluating the resulting number of elements based on the rate of phase variation on the transducer surface; therefore a rapid computational method for obtaining the rate of phase variation is desirable. Such a rapid method is provided as part of the subject invention in the form of backprojection ray tracing. According to this method, and referring to FIG. 3, one can determine the required phase variation for an aperture 64 located on the probe surface 40 that can produce a predetermined beam diameter at a desired focal point 51 along reverse incident unit vector 55. In the backprojection ray-tracing method, the beamwidth half-angle 53 is used, or if it is not known, the beamwidth half-angle 53 is derived from the predetermined beam diameter value, and a beam cone with the derived half-angle is backprojected through the media 43, 42 and 41, and across the interfaces 46 and 45, onto the probe surface 40 in the direction of the corresponding reverse incidence unit vector 53.

A plurality of rays uniformly spanning the cone associated with focal point 51 emerges from volume of interest 48 through region 58 onto the surface 49 of the volume of interest. The plurality of rays defines an intersection region 60 with interface 46 between media 43 and 42 at which point refraction occurs according to Snell's law and the different sound speeds in media 43 and 42. The plurality of rays associated with the cone continues until intersection with medium 45 between media 42 and 41, thereby defining an intersection region 62 on interface 45. Each ray in the plurality of rays refracts according to Snell's law and the sound speeds of media 42 and 41. Finally, the plurality of rays propagates in medium 41 until intersection with the probe surface 40 thereby defining an aperture 64 required to generate the desired beam diameter and incidence direction at focal point 51.

Each ray within the plurality of rays associated with the cone emanating from focal point 51 carries phase information describing the total phase between focal point 51 and intersection with the probe surface 40, including interactions with all intervening media and interfaces. Therefore, the plurality of rays, in aggregate, can be used to interpolate the phase between the focal point 51 and the transducer surface 40 at all points within aperture 64.

Similarly for focal point 52 of FIG. 3, one can determine the required phase variation for an aperture 65 located on the probe surface 40 that can produce a predetermined beam diameter at a desired focal point 52 along reverse incident unit vector 56. In the backprojection ray-tracing method, the beamwidth half-angle 54 is used, or if it is not known, the beamwidth half-angle 54 is derived from the predetermined beam diameter value, and a beam cone with the derived half-angle is backprojected through media 44, 43, 42 and 41, and across interfaces 47, 46 and 45, onto the probe surface 40 in the direction of the corresponding reverse incidence unit vector 56.

A plurality of rays (not shown, for clarity of illustration) uniformly spanning the cone associated with focal point 52 emerges from volume of interest 48 through region 57 on interface 47. Each ray in the plurality of rays refracts according to Snell's law and the sounds speeds of media 44 and 43. The plurality of rays then intersect the volume of interest inside region 59 and continue to define an intersection region 61 with interface 46 between media 43 and 42 at which point refraction occurs according to Snell's law and the different sound speeds in media 43 and 42. The plurality of rays associated with the cone continues until intersection with interface 45 between media 42 and 41, thereby defining an intersection region 63 on interface 45. Each ray in the plurality of rays refracts according to Snell's law and the sound speeds of media 42 and 41. Finally, the plurality of rays propagates in medium 41 until intersection with the probe surface 40 thereby defining an aperture 65 required to generate the desired beam diameter and incidence direction at focal point 52.

Each ray within the plurality of rays associated with the cone emanating from focal point 52 carries phase information describing the total phase between focal point 52 and intersection with the probe surface 40, including interactions with all intervening media and interfaces. Therefore, the plurality of rays, in aggregate, can be used to interpolate the phase between the focal point 52 and the transducer surface 40 at all points within aperture 65.

The apertures 64 and 65 from focal points 51 and 52 respectively are seen to overlap partially on transducer surface 40. In general, extending this process to many focal points within volume of interest 48, it is seen that many different overlapping apertures will exist on transducer surface 40, and that each one will possess its own phase variation associated with its focal point. At each point on the transducer surface 40, one of these apertures will generate the phase variation requiring the smallest element sizes. This aperture will be the one that generates the greatest absolute value of the phase rate on the transducer surface. In a general transducer surface Geometrical Design, in contrast to the one-dimensional simplification described below, the user is required to specify a parameterized family of curves to define the element boundaries. If the array is a two-dimensional array, the user is required to specify a second parameterized family of curves substantially perpendicular to the first family to define the element boundaries in the second dimension. The integral of the maximum rate of phase change perpendicular to each of the family of curves can be used to define the specific shapes of the boundaries and the number of elements.

The backprojection ray tracing method is illustrated in the presence of a mirror and lens in FIG. 4. For focal point 84, one can determine the required phase variation for an aperture 114 located on the probe surface 110 that can produce a predetermined beam diameter at a desired focal point 84 along reverse incident unit vector 88. In the backprojection ray-tracing method, the beamwidth half-angle 86 is used, or if it is not known, the beamwidth half-angle 86 is derived from the predetermined beam diameter value, and a beam cone with the derived half-angle and containing a plurality of rays uniformly spanning the cone is backprojected in the reverse direction of the corresponding reverse incidence unit vector 88 through medium 80, until intersection with interface 82 in intersection region 90. Each ray in the plurality of rays is refracted according to Snell's law and the sound speeds in media 80 and 111. The rays backpropagate to the mirror 92 in intersection region 96. Each ray in the plurality of rays inside the beam cone is then reflected specularly from mirror 92, and projected through medium 111 to lens 98. The beam cone intersects lower interface 100 of lens 98 in intersection region 106 and each ray in the plurality of rays refracts according to Snell's law and the sound speeds in media 111 and 98. The rays pass through lens 98 and intersect the upper interface 102 of the lens 98, in intersection region 108. Each ray in the plurality of rays then refracts according to Snell's law and the sound speeds of media 98 and 111. Finally, the plurality of rays backpropagate in medium 111 until intersection with the probe surface 110 in intersection region 114.

Each ray within the plurality of rays associated with the cone emanating from the focal point 84 carries phase information describing the total phase between the focal point 84 and intersection with the probe surface 110, including interactions with all intervening media, acoustic mirrors and/or acoustic lenses. Therefore, the plurality of rays, in aggregate, can be used to interpolate the phase between the focal point 84 and the transducer surface 110 at all points within aperture 114. As before, the required number of elements on the transducer surface can be determined from families of curves defining element boundaries and the integral of the maximum absolute value of phase rate along directions substantially orthogonal to the element boundary curves.

In the general formulation discussed above and depicted in FIGS. 3 and 4, the Geometrical Design is inherently a two-dimensional problem involving unknown attributes of a surface. Parameterization of a two-dimensional surface and of two-dimensional array shapes and boundaries requires a great number of parameters resulting in a potentially slow convergence of the optimization method to the global minimum of the Global Cost. Additionally, solving for the value of the Global Cost at each iteration in flowchart 20 is costly because computations in three dimensions are required to handle ultrasonic propagation to and from two-dimensional surfaces. This invention is not specific to any particular technique for parameterizing surfaces. What is required is that some parameters are available to the optimization routine so that, in changing the value of such parameters, the Geometrical Design, and more specifically the transducer shape, may be changed. Commonly, products of polynomials and cosine series each with unknown coefficients generate useful transducer shapes for the purposes of ultrasonic insonification.

In some Geometrical Design problems, the Basic Problem Statement, Insonification Requirements and Geometrical Constraints imply symmetry about one or more planes, or symmetry about an axis. In such cases, according to the present invention, the Geometrical Design is simplified to a one-dimensional optimization problem involving fewer parameters than a two-dimensional case, resulting in a significant increase in the convergence rate of the optimization method to the global minimum.

Figure 5:
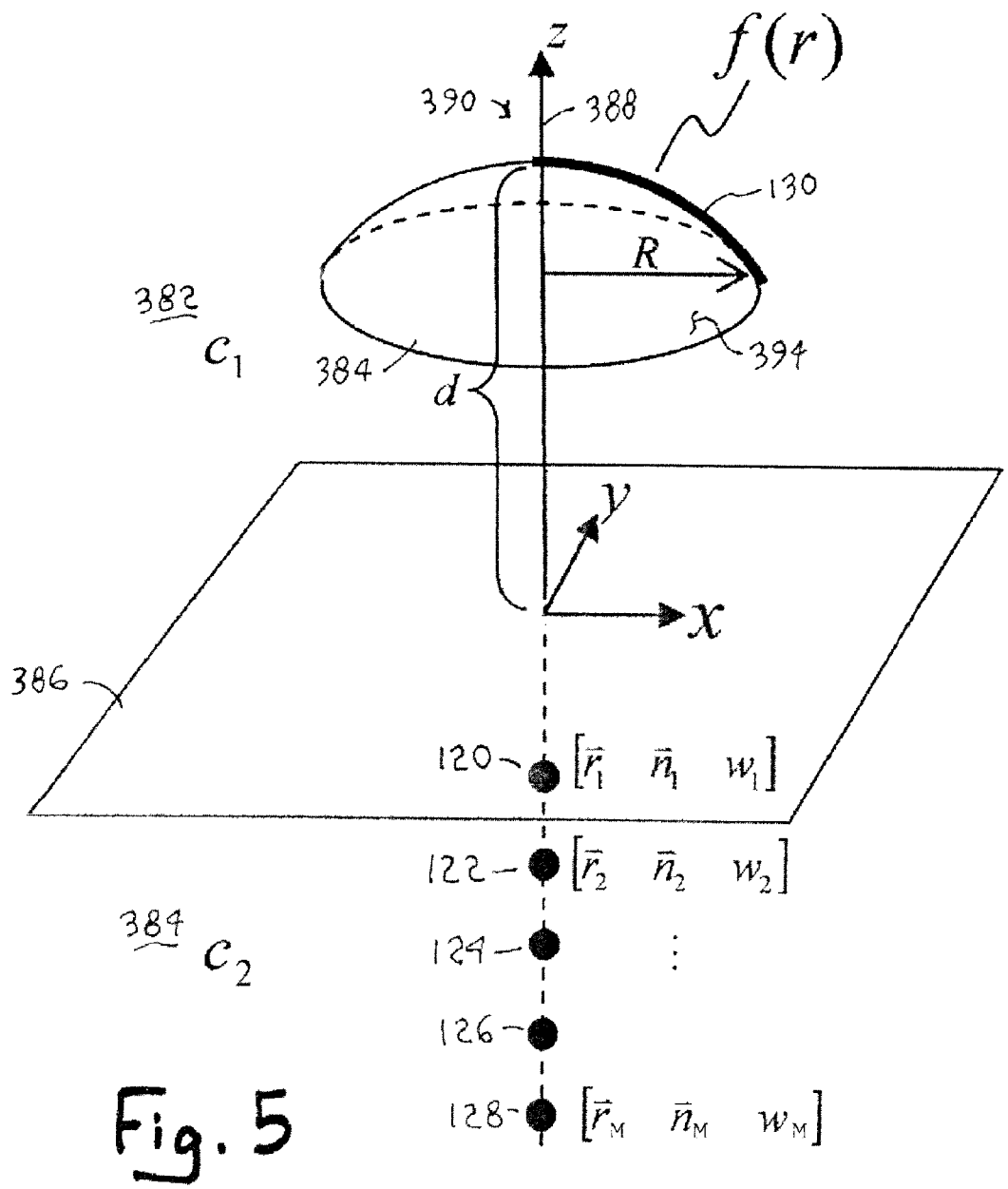
FIG. 5 is a schematic diagram of a system and method providing for the normal incidence of inspection within one medium using an axisymmetric array in a different medium.

We now illustrate the one-dimensional embodiment of the present invention. Consider the transducer design scenario of FIG. 5. The Basic Problem Statement involves media 382 and 384 separated by flat interface 386. A Cartesian coordinate system 390 is positioned and oriented such that the flat interface 386 is coincident with the plane z=0. The volume of interest is medium 384. The relevant physical properties are the sound speed in medium 382, $c_1$, and the sound speed in medium 384, $c_2$.

The Insonification Requirements consist of a set of M discrete focal points 120 through 128 along the z-axis. The discrete focal points 120 through 128 are here denoted by the expressions [$\vec{r}_i$, $\vec{m}_i$, $w_i$], i=1, 2, ... M, with $$\vec{r}_i = [0 \ 0 \ -d_i], d_i > 0, \quad (3)$$
$$\vec{n}_i = [0 \ 0 \ -1], \text{ and}$$
$$w_i = const = w.$$

The Insonification Requirements also include the center frequency.

The Geometrical Constraints consist of (i) forcing the intercept of the z-axis 388 with transducer surface 394 to be equal to d; (ii) forcing all points on surface 394 to lie above interface 386; and (iii) enforcing the gradient of surface 394 to be zero at the intercept of z-axis 388 with the surface 394.

The Basic Problem Statement, Insonification Requirements, and Geometrical Constraints imply that there exists an axis of symmetry consisting of the z-axis 388. In accordance with the present invention, transducer surface 394 can therefore be simplified to a one-dimensional profile 130 described mathematically as f(r) to accelerate the convergence of the optimization method. The full two dimensional transducer shape 394 can be constructed at any time as a surface of revolution by revolving profile 130 about axis of symmetry 388. In this example, the geometrical features of interest as part of the Geometrical Design are the profile f(r) and the breaks $b_k$ (described below) on f(r) delimiting the element boundaries. The two dimensional shapes of the elements will be rings by axial symmetry.

We also note that the constraint of no collision with the interface and the constraint on the standoff distance respectively can be given by the expressions, $$f(r) > 0 \text{ and } f(0) = d. \quad (4)$$

Figure 6:
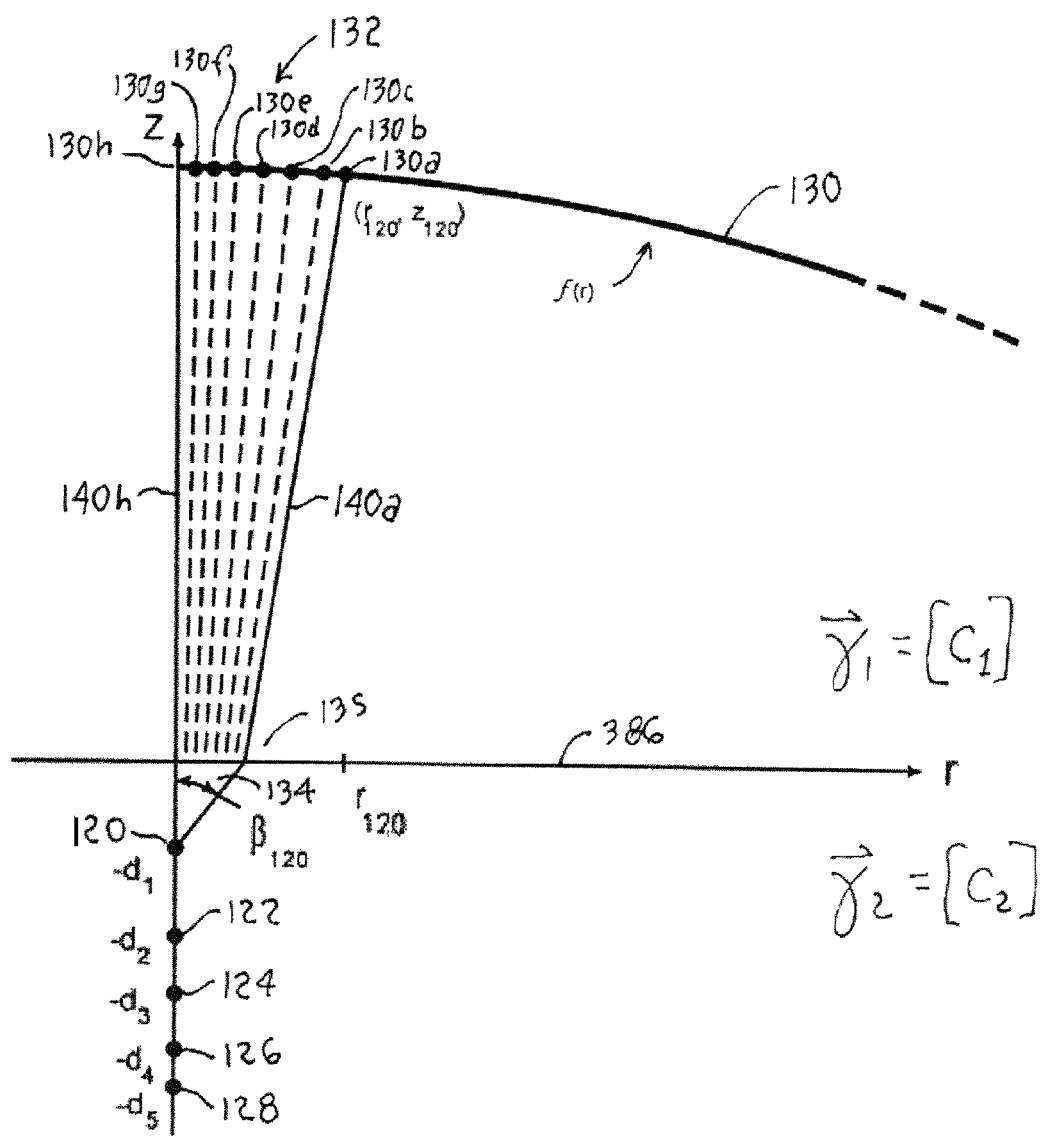
FIG. 6 is a schematic diagram illustrating a backprojection ray tracing method used to derive phase information for a first focal point in the system of FIG. 5.

For simplicity we specify a single Optimization Attribute to be minimized, which is the number of elements on the array. The backprojection ray tracing method discussed earlier can be adapted to a one-dimensional scenario and can yield the necessary phase information to determine the number of elements for each candidate shape f(r), or mathematical curve, whose shape is to be determined in accordance with the present invention. An aperture 132, shown in FIG. 6, is used to produce the requisite beam 134 at the first focal point 120, where the beam 134 has a half-angle) $\beta_{120}$ which is the one-dimensional analog to the cone half angle of the previously described backprojection ray-tracing technique. The aperture 132 includes the profile points 130a through 130h, where the profile point 130a is defined by the coordinate pair ($r_{120}$, $z_{120}$), and the profile point 130h is defined by the coordinate pair (0, $z_{120}$).

Figure 7:
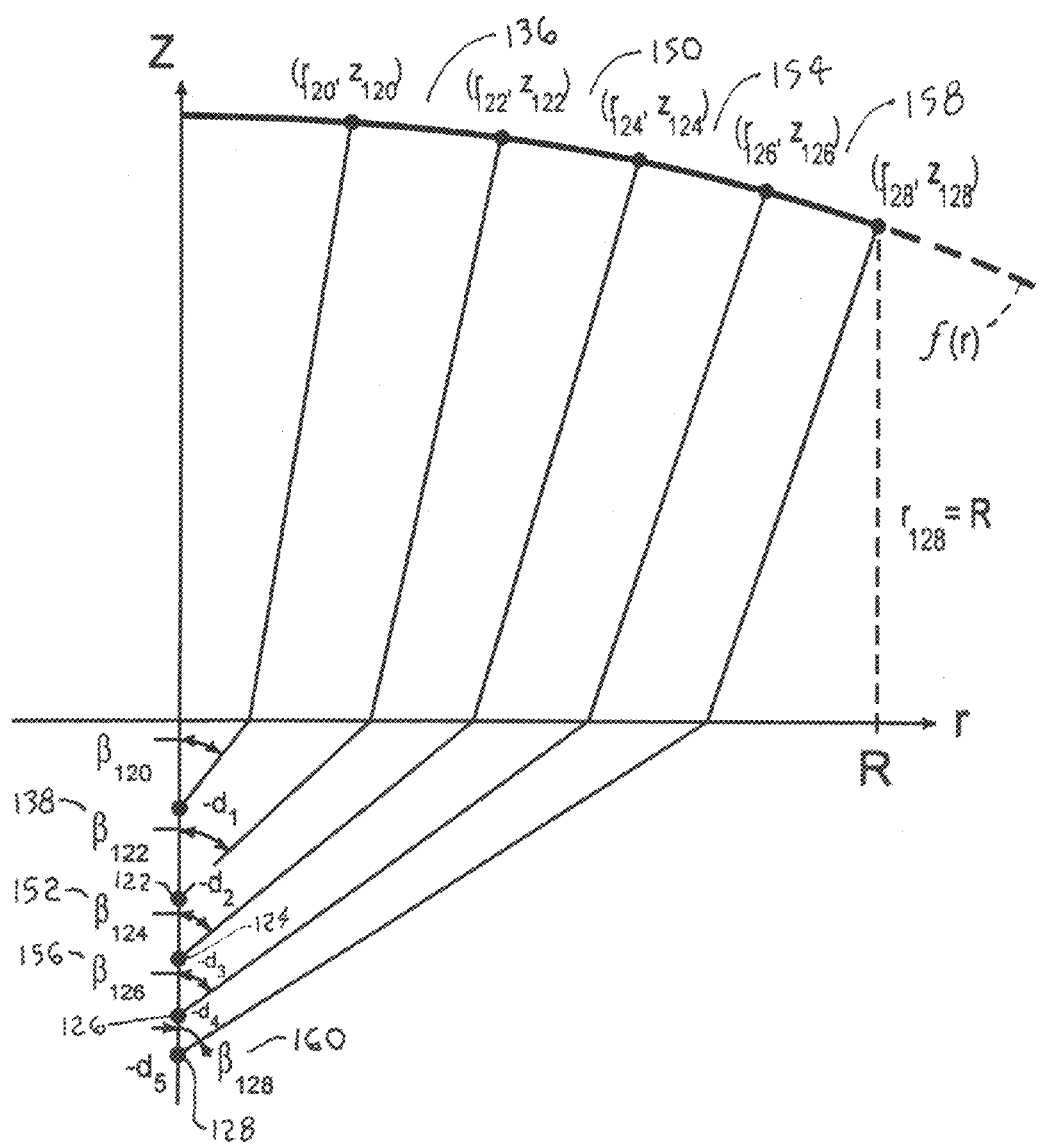
FIG. 7 is a schematic diagram illustrating backprojection ray tracing used to derive phase information for four inspection points in the system of FIG. 5.

A phase distribution across the aperture 132 is obtained by calculating the total phase along the rays 140a through 140h which link focal point 120 and the respective profile points 130a through 130h. The phase distribution can be obtained by either specifying the profile points on the aperture and deriving the phase values by means of the plurality of eigenrays 140a through 140h each satisfying Snell's Law at interface 135, or by defining the rays 140a through 140h and deriving the respective profile points 130a through 130h by intersecting interface 135, refracting each ray according to Snell's Law, and then intersecting transducer profile 130. The process is repeated for each of the apertures associated with the other focal points 122, 124, 126, and 128, as shown in the diagrammatical illustration of FIG. 7.

An aperture 136 is used to produce the requisite beam 138 at the second focal point 122, where the beam 138 has a half-angle) $\beta_{122}$. Similarly, an aperture 150 is used to produce the requisite beam 152 at the third focal point 124, where the beam 152 has a half-angle) $\beta_{124}$, an aperture 154 is used to produce the requisite beam 156 at the fourth focal point 126, where the beam 156 has a half-angle) $\beta_{126}$, and an aperture 158 is used to produce the requisite beam 160 at the fifth focal point 128, where the beam 160 has a half-angle) $\beta_{128}$.

Figure 8:
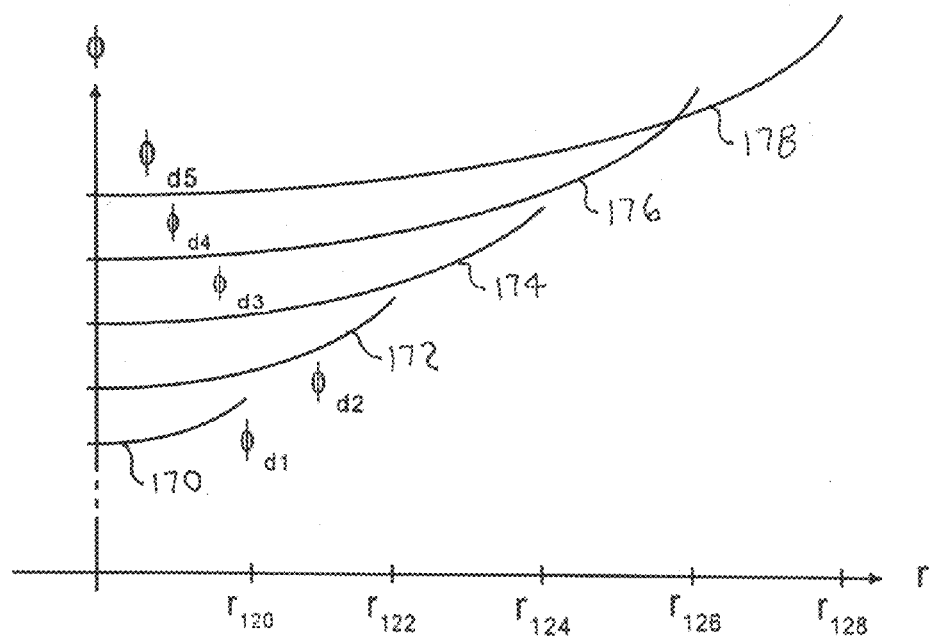
FIG. 8 is a graph showing five phase curves corresponding to the five focal points of FIG. 6 and derived from phase information obtained using the backprojection ray tracing method of FIG. 7.
Figure 9:
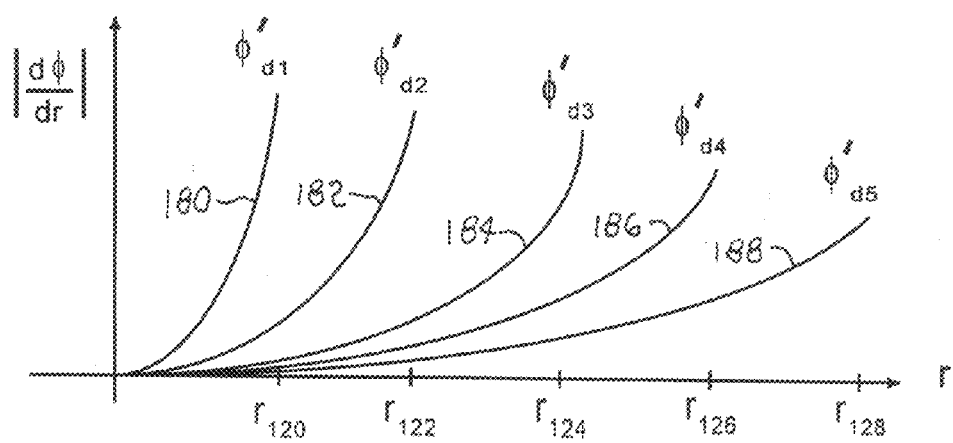
FIG. 9 is a graph showing a family of phase rate change curves derived from the five phase curves of FIG. 8.
Figure 10:
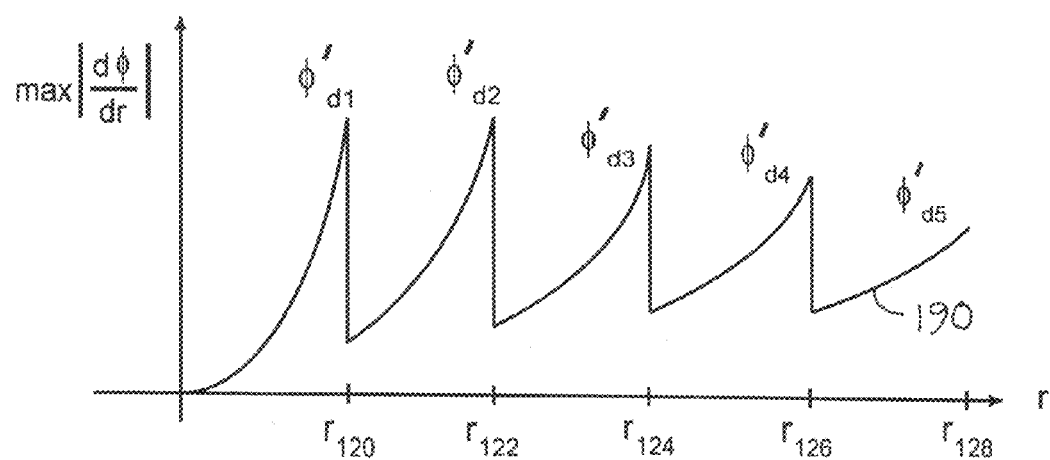
FIG. 10 is a graph showing a composite phase rate change curve of maximum phase rates as a function of distance along the profile derived from the five phase rate change curves of FIG. 9.
Figure 11:
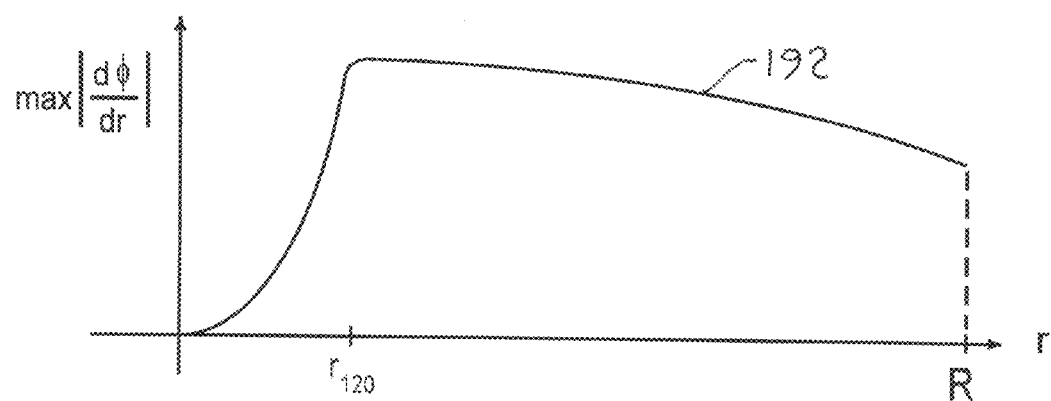
FIG. 11 is a composite graph comprising a phase rate change curve derived from a large plurality of focal points.

The resulting phase distribution values within each of the apertures 132, 136, 150, 154 and 158 can be plotted as a family of phase curves 170 through 178, shown in FIG. 8. Each phase curve begins as r=0 and extends until the end of its respective aperture. As one would expect, the phase intercept at r=0 grows larger for the deeper focal points because the total path length is greater. The phase curves 170 through 178 can be used to obtain a family of corresponding phase rate curves 180 through 188, shown in FIG. 9. The phase rate curves 180 through 188 can then be used to obtain a composite phase rate change curve 190 of maximum phase rate $$\left(\text{i.e., } \max\left|\frac{d\phi}{dr}\right|\right)$$

as a function of distance r along the profile 120, shown in FIG. 10. In the example provided, the composite graph 190 has been derived from a set of five focal points, where the corresponding maximum phase rate values are denoted by $\phi'_{d1}$, $\phi'_{d2}$, $\phi'_{d3}$, $\phi'_{d4}$, and $\phi'_{d5}$. As the number of focal points used in the derivation is increased, the resulting composite phase rate change values approaches the composite graph 192 shown in FIG. 11.

Figure 12:
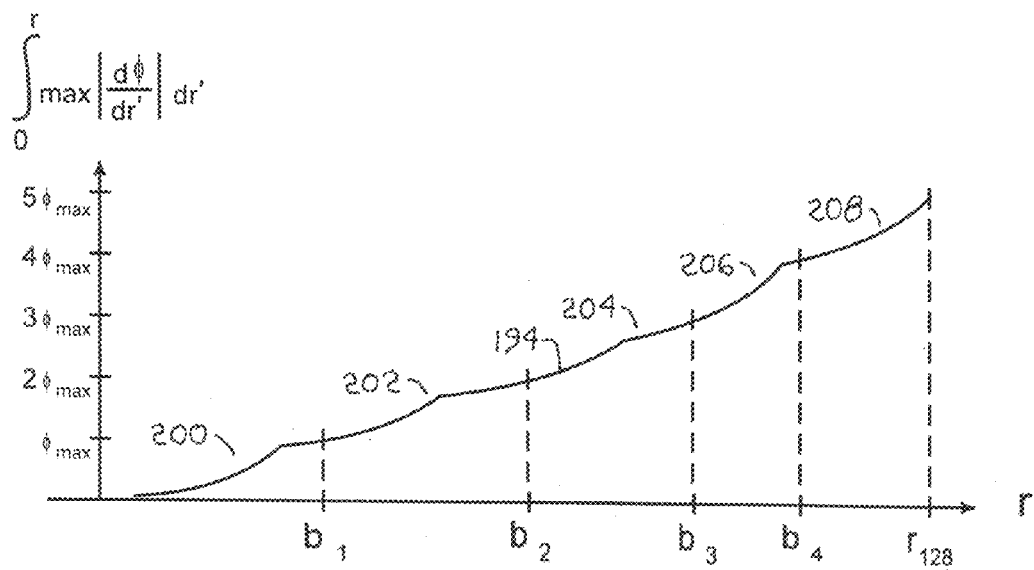
FIG. 12 is a composite phase curve obtained from integrating the composite phase rate change curve of FIG. 10.

The composite phase rate change curve 190 can be integrated to produce a composite phase curve 194, shown in FIG. 12. The composite phase curve 194 may then be utilized to determine the number of transducer elements required for the current Geometrical Design, i.e. the shape of f(r). A maximum tolerable phase variation per element $\phi_{max}$ is specified. As discussed earlier, it is common to specify that the phase variation per element not exceed 60° (i.e., $$\left(\text{i.e., } \frac{\pi}{3} \text{ radians}\right).$$

radians). multiples of the specified maximum phase variation value may be plotted on the vertical axis, and the corresponding profile break points $b_1$, $b_2$, $b_3$, and $b_4$ can be identified on the horizontal axis. In the example shown, five transducer elements, represented by segments 200, 202, 204, 206, and 208 will provide the insonification parameters specified for the ultrasonic transducer configuration of FIG. 6, described above.

Figure 13:
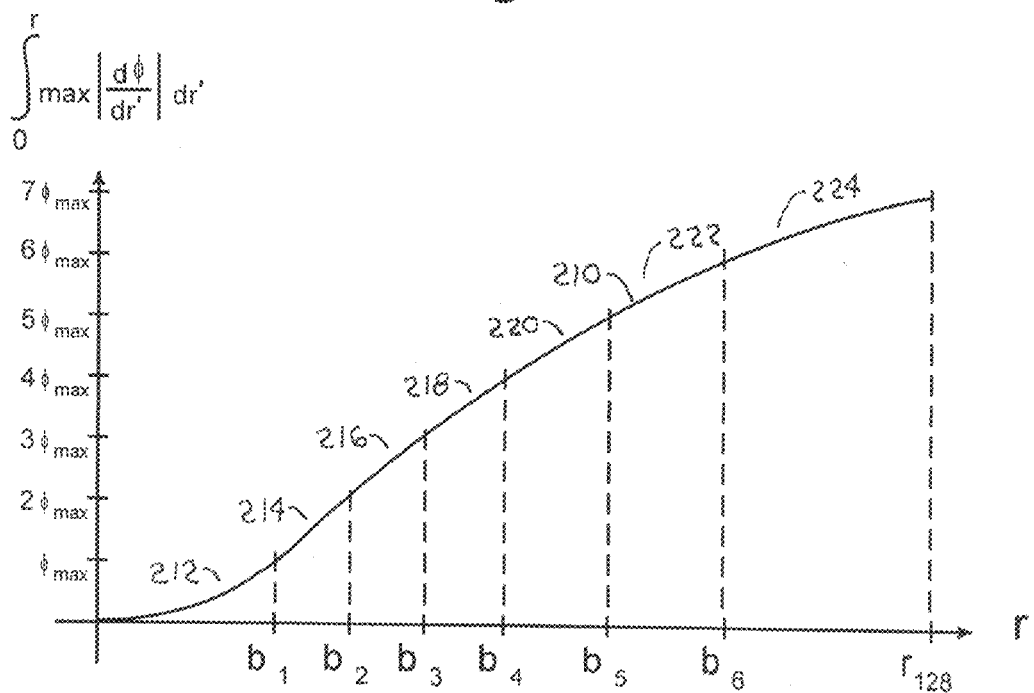
FIG. 13 is a composite phase curve obtained from integrating the composite phase rate change curve of FIG. 11.

Similarly, the composite phase rate change curve 192 can be integrated to produce a composite phase curve 210, shown in FIG. 13. In this example, seven transducer elements, represented by segments 212, 214, 216, 218, 220, 222, and 224, are used. Mathematically, the procedure described above states that the profile $f_{OPT}r)$ yielding the minimum number of elements is $$f_{OPT}(r) = \underset{f(r)}{\arg\min} \int_0^R \underset{i=1}{\overset{M}{\max}} \left| \frac{d\phi_{d_i}}{dr'} \right| dr'. \quad (5)$$

where M=5 in the example of FIG. 12. In an exemplary embodiment, consistent with the continuous slope required, the profile 130 can be represented by a polynomial expression of degree P:

$$f(r) = \sum_{p=0}^P \alpha_p r^p. \quad (6)$$

The polynomial representation in Equation (6) also simplifies the optimization in Equation (5) to a search over P+1 coefficients:

$$\{\alpha_i\}_{OPT} = \underset{\{\alpha_i\}}{\arg\min}\left( \int_0^R \underset{i=1}{\overset{M}{\max}} \left| \frac{d\phi_i}{dr} \right| dr \right). \quad (7)$$

Figure 14:
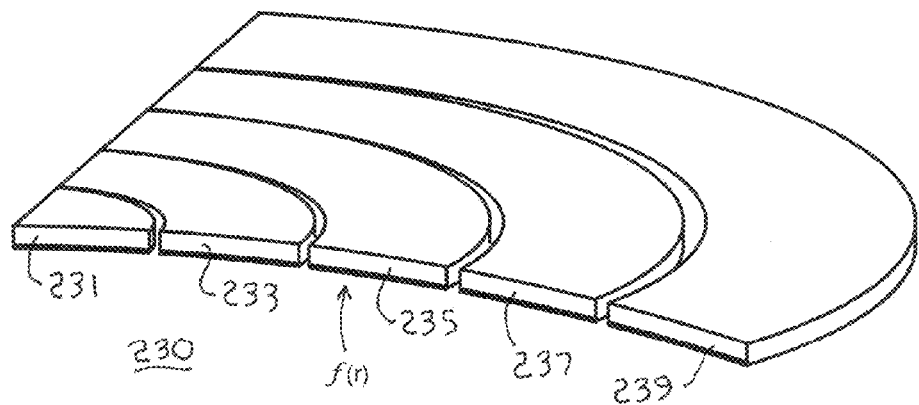
FIG. 14 is a partial diagrammatical view of a circular probe comprising annular segments based on five transducer elements derived by means of the composite phase curve of FIG. 12.

In this axis-symmetric example, the two-dimensional annular ultrasonic transducer design based on the five transducer elements derived in FIG. 12 may be configured by rotating the segmented profile 130 about the axis of symmetry 388 to produce a circular probe 230 comprising annular segments 231, 233, 235, 237, and 239, partially shown in FIG. 14.

Figure 15:
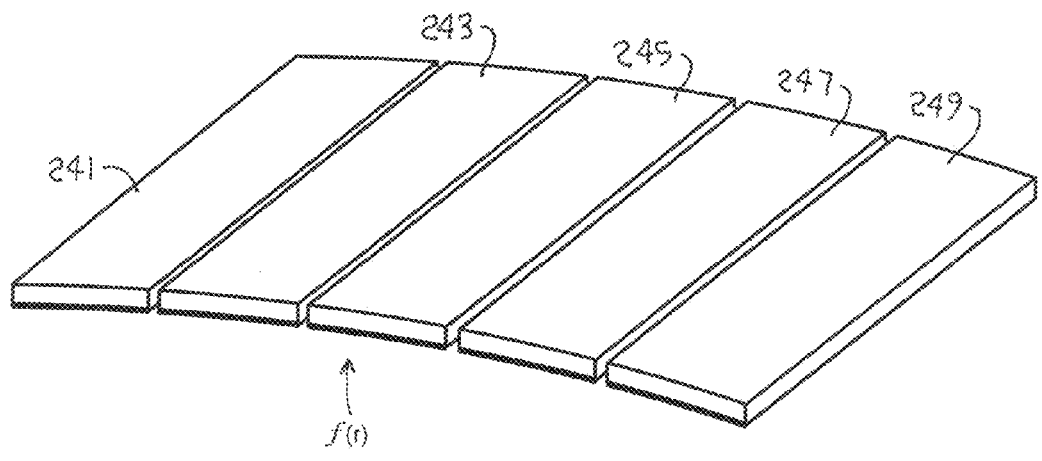
FIG. 15 is a partial diagrammatical view of a linear transducer array comprising segments based on five transducer elements derived by means of the composite phase curve of FIG. 12.

Although we do not show a detailed example of a one-dimensional profile resulting from the existence of a plane of symmetry rather than an axis of symmetry, FIG. 15 shows that in such a case the segmented profile 130 would be translated along an axis perpendicular to the plane containing the segmented profile 130 produce a linear transducer array 240 comprising segments 241, 243, 245, 247, and 249. Focusing points in this case ideally all lie in the plane of symmetry, since the resulting linear array will have no ability to focus in a direction perpendicular to this plane.

The ultrasonic probe design process described with reference to FIGS. 6 through 13 can be summarized in the flow diagram 250, shown in FIG. 16, where the flow diagram 250 comprises a more detailed description of step 26 of the flow diagram 20, described above. The phase values on the profile 130 are calculated for each focusing point, at step 252. The absolute value of the rate of change of the phase along the profile 130 is calculated from the phase value calculations, at step 254. The maximum absolute value is found, for each value of r, among the focal points specified, at step 256. The maximum absolute phase values are integrated, at step 258, to produce a maximum phase distribution, which may be used to determine the number of transducer elements needed to satisfy the Basic Problem Statement.

Figure 16:
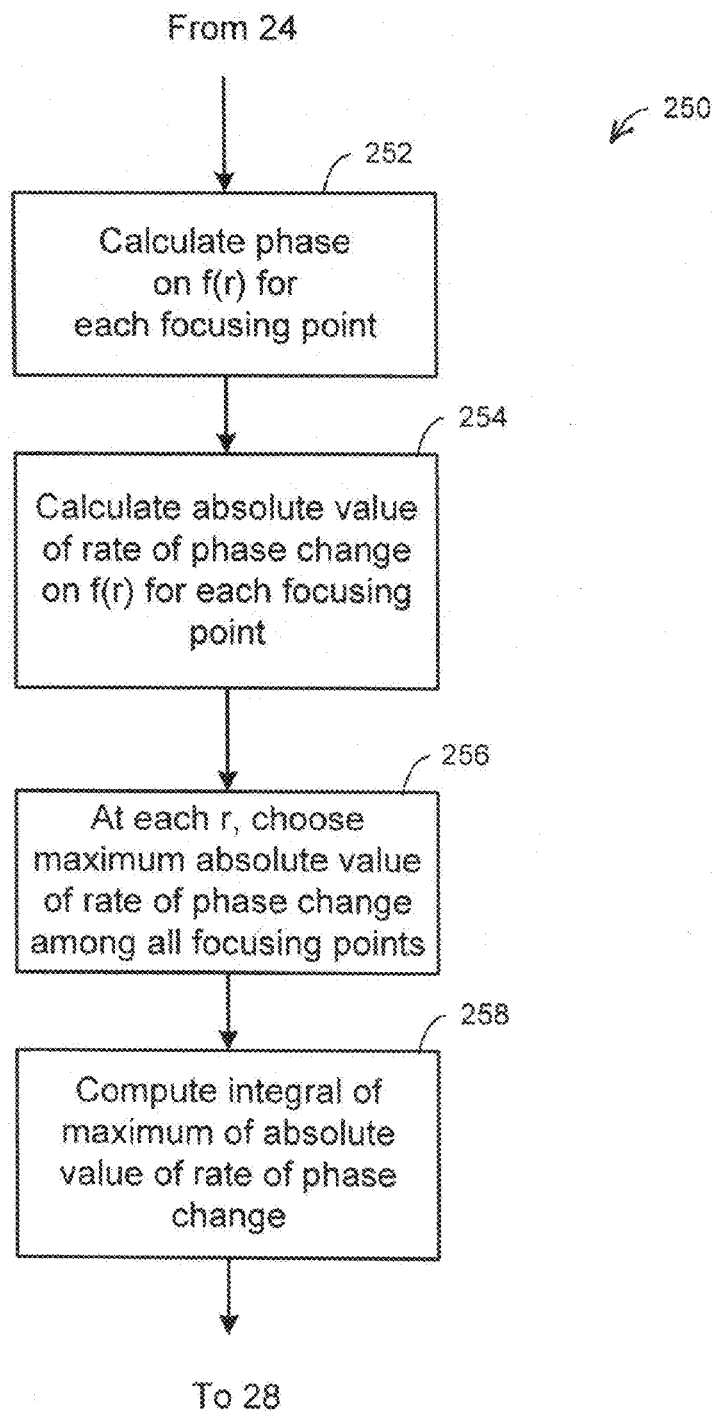
FIG. 16 is a process flow diagram including steps corresponding to the probe design process illustrated in FIGS. 6 through 13.

To highlight the benefit of the optimization method, the probe design computed according to method 250, FIG. 16, is compared with two commonly used annular array shapes: flat and Fermat focused. For the purposes of this comparison we assign specific values to all the parameters needed to run engine 14, FIG. 1. Medium 82 is water with $c_1$=1500 msec and medium 84 is a solid whose longitudinal wave speed is $c_2$=6000 msec; the signal is a Gaussian pulse with a 6-dB bandwidth of 70% and a center frequency of 10 MHz; the water path is d=50 mm; the constant value of 6-dB beamwidth we seek is w=1 mm; the number of depth points is 6, with the following individual depth values of the focusing points; $d_1$=12.5 mm, $d_2$=25 mm, $d_3$=37.5 mm, $d_4$=50 mm, $d_5$=62.5 mm and $d_6$=75 mm. Finally, the order of the polynomial representation of f(r) is P=5.

The Fermat focused probe is designed to produce spherical focusing at 75 mm depth into medium 84 and is numerically generated using constant phase backprojection ray-tracing. In the present case, it turns out that the departure of the Fermat surface from a spherical cap is minimal, so the Fermat array shape could in fact be referred to as spherical.

Figure 17:
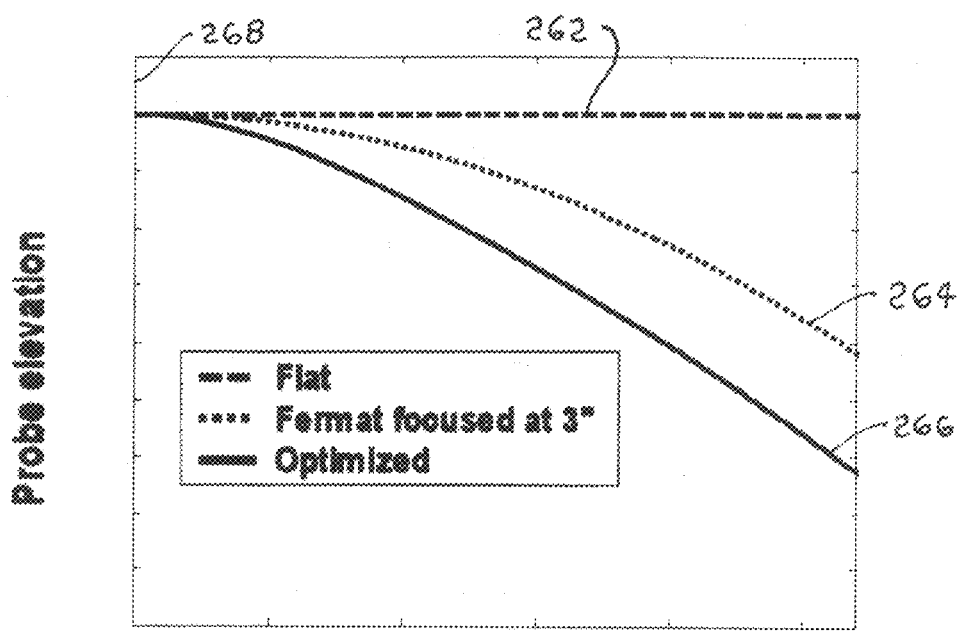
FIG. 17 is a graph providing a comparison of the respective radial profiles of a flat probe, a Fermat focused probe, and a probe design computed in accordance with the process flow diagram steps of FIG. 16.

FIG. 17 is a graph 260 providing a comparison of the radial profile f (r) for the three probes, demonstrating that each profile is, on the scale of the wavelength, significantly different from the other profiles. FIG. 17 is a plot of a flat probe profile 262, a Fermat focused probe profile 264, and an optimized probe profile 266. The vertical axis 268 is amplified to highlight the differences, which are several wavelengths λ in magnitude. The wavelength is taken at the center frequency of 10 MHz in water. FIGS. 18-20 compare the required phase of each of the arrays at the six focusing depths. The Fermat focused probe phase variation approaches zero as the focusing point gets deeper, from FIG. 19A to FIG. 19B, as one would expect given that this probe is naturally focused at the deepest point. This exceptional performance at the deepest points is unfortunately counter-balanced by poor performance at the shallow points. On the other hand, the optimized array's shape places the least strain on focusing overall.

Figures 18A, 18B, 18C:
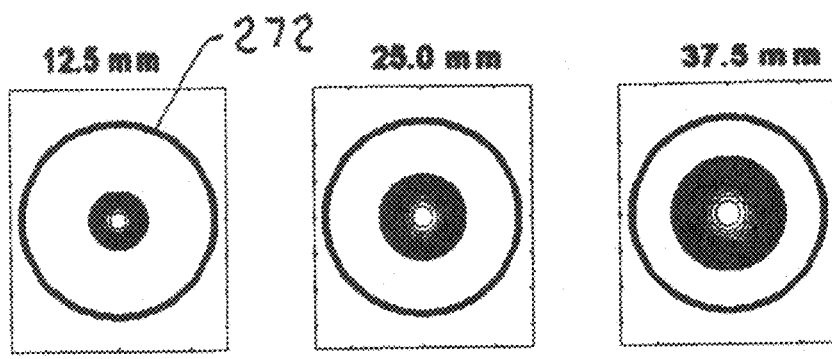
FIGS. 18A-F are illustrations of the required phase variation at six focusing depths for the flat probe of FIG. 17.
Figures 18D, 18E, 18F:
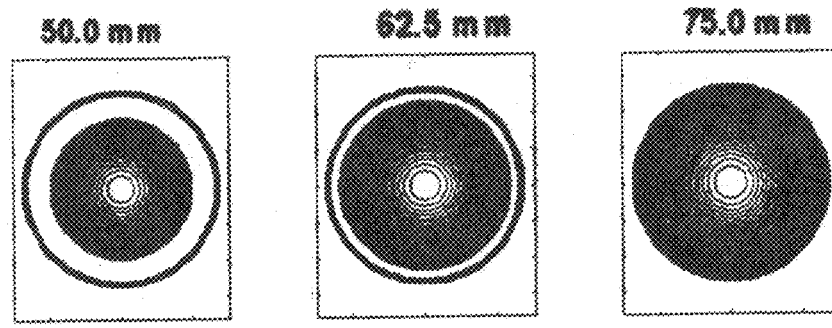

FIGS. 18-20 are backprojection ray-tracing to flat (FIGS. 18A-18F), Fermat focused (FIGS. 19A-19F), and optimized (FIGS. 20A-20F) probes for the six depth points in the numerical study. Each ray-trace result depicts a number of thin contours at phase intervals of 60 degrees, as well as two thick contours. The inner thick contour is the boundary of the required aperture for the current depth point, while the outer thick contour is constant and represents the probe boundary, as required to accommodate the deepest inspection point. Note the relatively large number of contours for the flat probe 272, and the relatively small number of contours for the optimized probe 276. It is also interesting to note the absence of any contours for the Fermat focused probe 274 at the 75 mm depth point, FIG. 19F, as should be the case since this point is the probe's natural focus. Axis units are millimeters.

The required number of rings for each of the arrays in FIGS. 18-20 is governed by the maximum phase experienced at each point on the respective probe face, over all the focusing conditions. Consider the Fermat focused phase diagrams of FIGS. 19A-19F. The maximum phase variation for central points comes from the 12.5 mm depth case. As the radius increases beyond the aperture for the 12.5 mm case, the maximum phase variation comes from the next deepest point.

Figure 21:
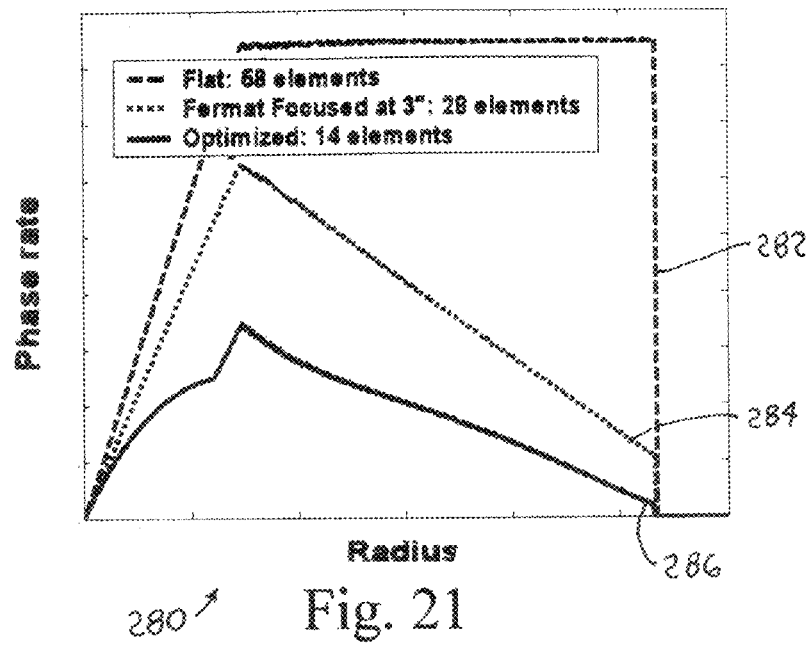
FIG. 21 is a graph providing a comparison of the respective maximum phases as a function of radius for the flat probe, the Fermat focused probe, and the probe design computed in accordance with the process flow diagram steps of FIG. 16.

A plot of maximum phase as a function of radius for the three probe types shown in FIGS. 18-20 is shown in a graph 280 in FIG. 21. The maximum phase at each radius, $$\underset{i=1}{\overset{M}{\max}}|d\phi/dr|,$$

is shown for a flat probe 272 as curve 282, for a Fermat focused probe 274 as a curve 284 and for an optimized probe 276 as curve 286. The number of elements can be readily deduced, in accordance with the disclosed method, by integrating each curve and dividing by the maximum allowable phase variation per element, which we have chosen to be 60 degrees. The optimized probe 276 comprising fourteen elements reduces the number of elements by 50% compared to the Fermat focused probe 274 comprising twenty-eight elements, and by 76% compared to the flat probe 272 comprising sixty-eight elements. By inspection, it can be seen that the optimized probe curve 286 has the lowest maximum phase rate at each value of radius. To generate FIG. 21, a large number of depth points were used to simulate continuous specification of one millimeter beamwidth from 12.5 mm to 75 mm depth. Without this continuous specification, the maximum phase curves would have contained discontinuities each time the depth point generating maximum changed discretely. The same kind of continuous specification could in theory have been used in the numerical optimization instead of using six discrete points, $d_1$=12.5 mm through $d_6$=75 mm. However, such a large number of depth points may be computationally prohibitive.

Figures 23A, 23B:
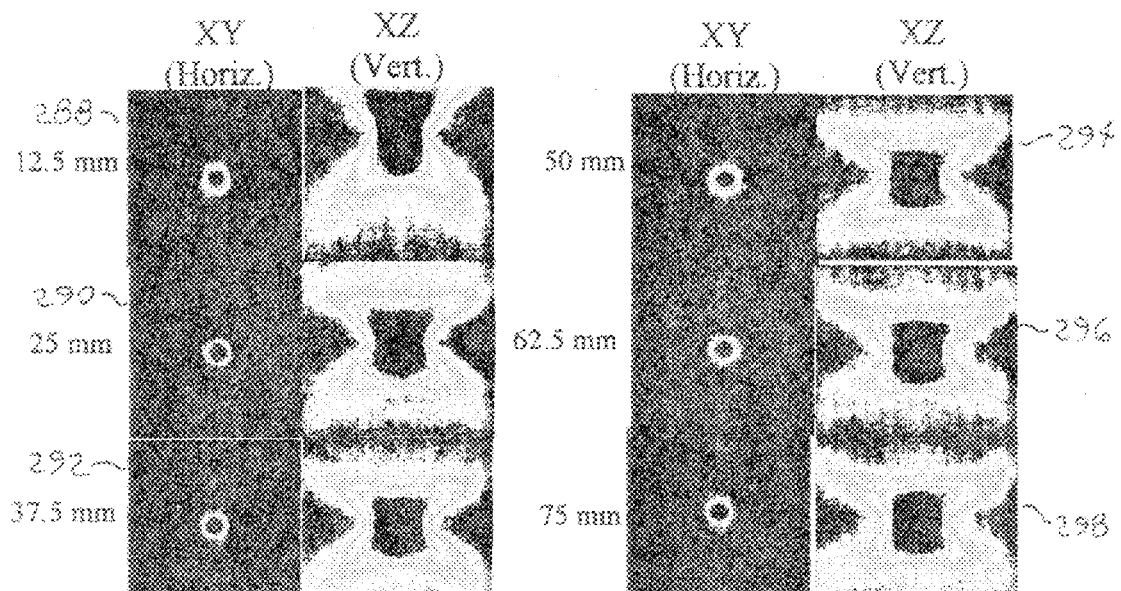
FIGS. 23A-B are illustrations verifying the design of the probe computed in accordance with the process flow diagram steps of FIG. 16.
Figure 22A:
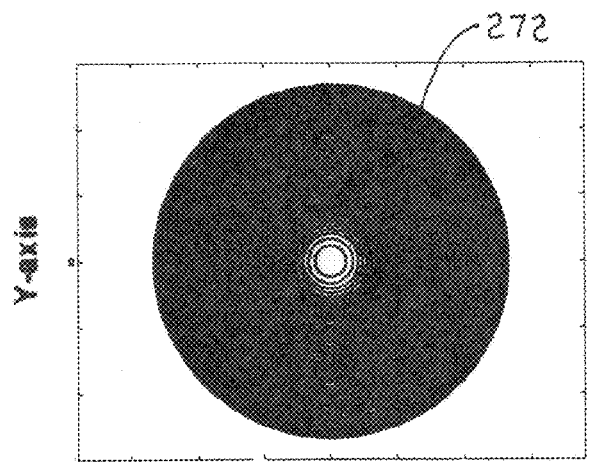
FIGS. 22A-C are respective depictions of ring boundaries for optimal segmentation of the flat probe, the Fermat focused probe, and the probe design computed in accordance with the process flow diagram steps of FIG. 16.
Figure 22B:
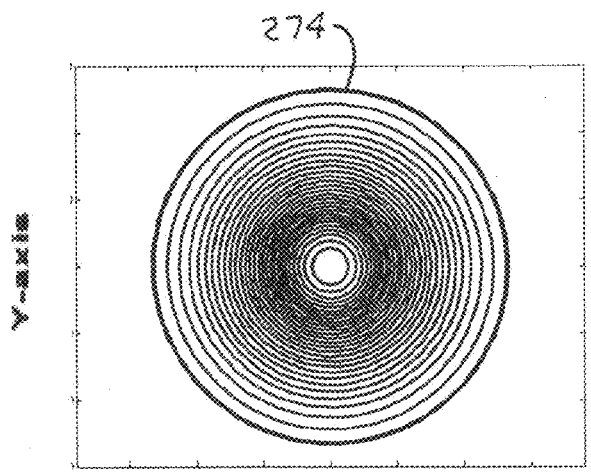
Figure 22C:
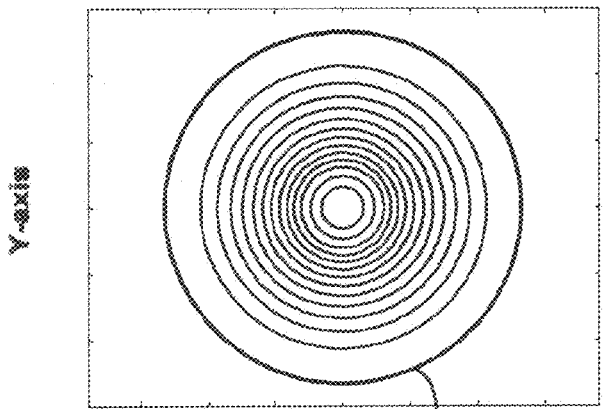

FIGS. 22A-22C depict the ring boundaries for optimal segmentation of the three arrays shown in FIGS. 18-20, in the sense that each ring is wide enough to accommodate precisely 60 degrees of maximal phase variation. FIGS. 22A-22C show optimal ring boundaries calculated according to the maximum phase rates, such as shown in FIGS. 12 and 13, assuming a 60 degree allowable phase variation per ring. As stated above, the flat probe 272, FIG. 22A, requires fifty-eight rings, the Fermat focused probe 274, FIG. 22B, requires twenty-eight rings, and the optimized probe 276, FIG. 22C, requires only fourteen rings to satisfy the inspection constraints of normal incidence, constant one millimeter beamwidth inspection throughout the depth range 12.5 mm to 75 mm. The optimized probe 276 thus requires 50% fewer rings than the Fermat focused probe 274, and 76% fewer rings than the flat probe 272. Design verification of the optimized probe 276 through modeling of the ultrasonic field at each depth point is shown in FIGS. 23A-23B. The ultrasonic field within medium 2 is modeled using the Acoustic Ideas Toolboxes for MATLAB, available from Acoustic Ideas, Wakefield, Mass., at each of the six required focusing depths 288-298. The horizontal and vertical longitudinal wave fields passing through each of the depth points are shown above. The measured 6-dB beamwidths are 1.10 mm±10% across all depths, demonstrating that the optimized array performs as intended despite a comparatively low number of rings.

The above example illustrates the effectiveness of the subject invention in the case of an axis-symmetric problem. There is another technique according to the subject invention for utilizing a one-dimensional transducer profile f(r) rather than a full two-dimensional description, even when the Basic Problem Statement presents no symmetry. The method described herein according to the subject invention does require that the Insonification Requirements present axial symmetry.

Figure 24:
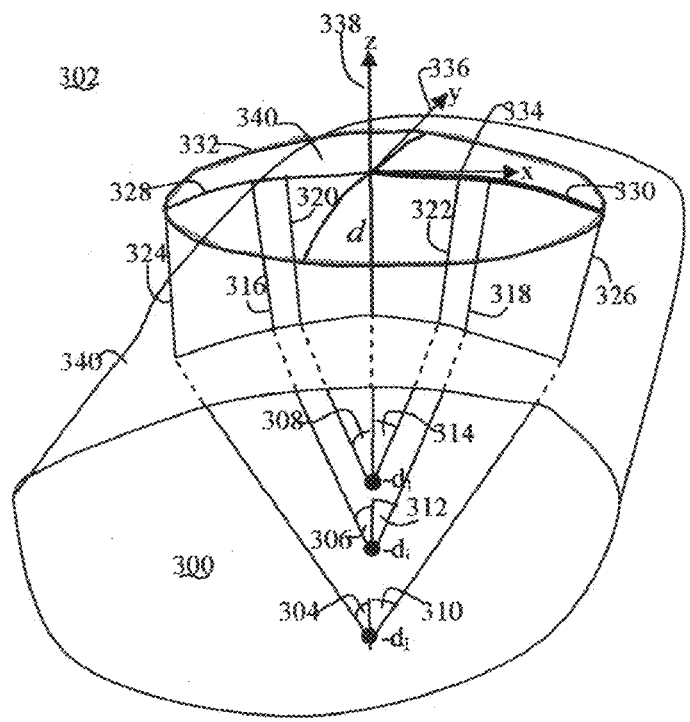
FIG. 24 is a diagrammatical depiction of the main aspects of a Basic Problem Statement and Insonification Requirements for a transducer Geometrical Design problem involving an irregularly shaped medium and a bounding surface surrounded by a coupling medium.

Consider the Basic Problem Statement for the example illustrated in FIG. 24, which consists of irregularly shaped medium 300 with sound speed $c_{300}$ and bounding surface 340 surrounded by coupling medium 302 with sound speed $c_{302}$. The volume of interest is medium 300, which is not symmetrical about any plane or axis. The Insonification Requirements consist of "I" focusing points $-d_1$ to $-d_I$ within the medium 300 along z-axis 338 requiring normal incidence insonification (along the z-axis 338) and specified values of beam diameter at each focusing point. The center frequency of the signal is also specified as part of the Insonification Requirements. The Insonification Requirements are symmetrical about an axis, which is the requirement for technique described in FIG. 24 to function as intended.

Geometrical Constraints are (i) a prescribed intersection of transducer surface 340 with z-axis 338 equal to d, and (ii) no intersection of transducer surface 340 with medium 300. The Optimization Attribute is the number of elements, which is to be minimized.

Figure 25:
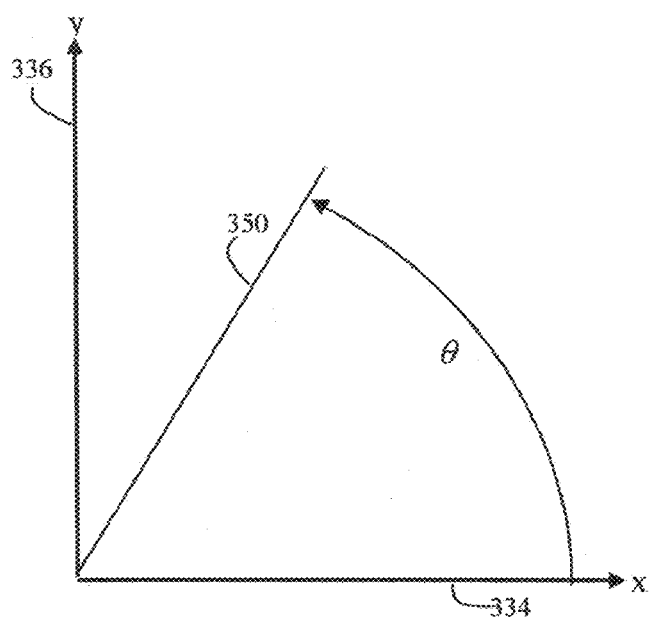
FIG. 25 is an illustration defining an eigenray making an azimuthal angle with the x-axis of a coordinate system used in FIG. 24.

The transducer design can be obtained without resorting to two-dimensional parameterizations of transducer surface 340. First, the problem is cast as a one-dimensional problem of finding transducer profile f(r), 330 using eigenrays 322, 318 and 326, in a manner analogous to the method illustrated in FIGS. 6-13. The projection of each eigenray 322, 318 and 326 on the x-y plane makes an azimuthal angle θ=0 with the x-axis, where θ is defined to be counter-clockwise from the x-axis 334 to a ray projection 350 in the x-y plane, as shown in FIG. 25. Once the transition profile 350 f(r) has been found, the full two-dimensional probe surface 340 is constructed through constant phase backprojection ray tracing. Specifically, the total phase along eigenray 322 corresponding to the focal point at $-d_1$ is recorded. Then, a second eigenray 320 is emanated from focal point $-d_1$ making an angle 308 with the z-axis 338 which is equal to angle 314. Eigenray 320 has an azimuthal angle θ=π. Eigenray 320 is propagated until it achieves the same phase as eigenray 322. The ending position of eigenray 320 is recorded as a point belonging to two-dimensional transducer surface 340 along θ=π.

Similarly, eigenray 316 is propagated from depth point $-d_i$ until it achieves the same phase as eigenray 318 connecting point $-d_i$ with profile f(r). Eigenray 316 makes an angle 306 with the z-axis which is equal to angle 312. This process is repeated for all I eigenrays, generating profile 328 along θ=π. By repeating the above steps at a large number of azimuthal values θ, and for a large number of profile rays I, a finely sampled array of points will be obtained lying on transducer surface 340. Interpolation or curve-fitting methods can then be used to continuously represent the transducer surface 340 at any point. It should be noted that the boundary 332 of the transducer surface 340 is generated as the convex hull of the array of points obtained through constant phase backprojection ray-tracing. It should also be noted that the central region of the transducer surface 340 can be defined by constant phase backprojection of a plurality of rays evenly distributed inside a cone with half angle 314.

The framework presented in this invention replaces the intuitive and iterative art of obtaining designs whose optimality cannot be guaranteed with a theoretical formulation ensuring mathematically optimal designs are more consistently achieved.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

While the invention has been described with reference to particular embodiments, it will be understood that the present invention is by no means limited to the particular constructions and methods herein disclosed and/or shown in the drawings, but also comprises any modifications or equivalents within the scope of the claims.

What is claimed is:

1. A method for optimizing an ultrasonic transducer design based on a one-dimensional profile curve and specified to produce one or more beams at one or more respective focal points in a volume of interest, said method comprising the steps of:

determining locations of a first through an N-th focal points with respect to a coordinate system;

specifying a first through an N-th beam parameters at respective said first through an N-th focal points;

establishing the location of the profile curve with respect to said coordinate system;

determining a first through an N-th apertures configured to produce said N beam parameters at respective said first through N-th focal points;

calculating a composite phase curve as a function of coordinate distance along the profile for said first through N-th apertures; and using said composite phase curve to derive one or more break points at respective one or more coordinate distance values along the profile curve, said one or more break points defining a segmented profile, the number of profile segments in said segmented profile determinant of an optimal value for the number of transducer elements in the ultrasonic transducer design.

2. The method of claim 1 wherein said step of calculating said composite phase curve comprises the steps of:

calculating a first through an N-th phase curves for each of respective said first through N-th apertures;

deriving a first through an N-th phase rate curves from said N phase curves;

deriving a composite phase rate change curve from said N phase rate curves; and integrating said composite phase rate change curve to produce said composite phase curve.

3. The method of claim 2 wherein said step of determining one or more said break points comprises the steps of:

specifying a maximum phase variation value for said transducer elements;

identifying a first break point at a first coordinate distance along the profile corresponding to a point on said composite phase curve having a value equal to said maximum phase variation value; and identifying additional break points at respective coordinate distances along the profile corresponding to points on said composite phase curve having values equal to multiples of said maximum phase variation value.

4. The method of claim 1 wherein the profile curve comprises a polynomial expression.

5. The method of claim 1 wherein said optimal value for the number of transducer elements in the ultrasonic transducer design is at least the number of said profile curve segments.

6. The method of claim 1 wherein the ultrasonic transducer design is configured by rotating said profile curve segments about an axis of symmetry.

7. The method of claim 1 wherein the ultrasonic transducer design is configured by translating said profile curve segments along an axis perpendicular to the plane containing said segmented profile.

8. A method for designing an ultrasonic transducer suitable for producing one or more specified beams at corresponding focal points in a volume of interest, said method comprising the steps of:

determining locations of the focal points with respect to the z-axis of a coordinate system;

backprojecting an eigenray from each of the focal points to produce a one-dimensional transducer profile, the projection of each said eigenray onto the x-y plane of said coordinate system oriented at a first azimuthal angle with the x-axis of said coordinate system; and constructing a two-dimensional probe surface from said one-dimensional transducer profile using constant phase backprojection ray tracing from the focal points.

9. The method of claim 8 wherein the focal points are on said z-axis.

10. The method of claim 8 wherein said step of constructing said two-dimensional probe surface comprises the step of backprojecting a second eigenray from each of the focal points to produce a second one-dimensional transducer profile, the projection of each said second eigenray onto said x-y plane oriented at a second azimuthal angle with said x-axis.

11. The method of claim 10 wherein the total phase along a second said eigenray propagated from a selected said focal point to said second one-dimensional transducer profile has the same value as the total phase along a first said eigenray propagated from said selected focal point to said first one-dimensional transducer profile.

* * * * *